US012752421B2

(12) United States Patent
Swarup et al.

(10) Patent No.: US 12,752,421 B2
(45) Date of Patent: Oct. 6, 2026

(54) DISTURBANCE COMPENSATION IN COMPUTER-ASSISTED DEVICES

(71) Applicant: INTUITIVE SURGICAL OPERATIONS, INC., Sunnyvale, CA (US)

(72) Inventors: Nitish Swarup, Sunnyvale, CA (US); Paul G. Griffiths, Santa Clara, CA (US); Goran A. Lynch, Tahoe City, CA (US); Daniel N. Miller, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/952,907

(22) Filed: Nov. 19, 2024

(65) Prior Publication Data

US 2025/0073899 A1 Mar. 6, 2025

Related U.S. Application Data

(63) Continuation of application No. 18/474,388, filed on Sep. 26, 2023, now Pat. No. 12,179,359, which is a (Continued)

(51) Int. Cl.

*G06F 17/00* (2019.01)
*A61B 34/30* (2016.01)

(Continued)

(52) U.S. Cl.

CPC ............. *B25J 9/1641* (2013.01); *A61B 34/30* (2016.02); *B25J 9/06* (2013.01); *B25J 9/1607* (2013.01);

(Continued)

(58) Field of Classification Search

CPC . B25J 9/1641; B25J 9/06; B25J 9/1607; B25J 9/1653; B25J 9/1682; B25J 19/0004;

(Continued)

(56) References Cited

U.S. PATENT DOCUMENTS

| | | | |
|---|---|---|---|
| 4,456,961 | A | 6/1984 | Price et al. |
| 4,625,837 | A | 12/1986 | Zimmer et al. |

(Continued)

FOREIGN PATENT DOCUMENTS

| | | | |
|---|---|---|---|
| CN | 1265057 | A | 8/2000 |
| CN | 1985773 | A | 6/2007 |

(Continued)

OTHER PUBLICATIONS

Vibration Prediction of the Robotic Arm Based on Elastic Joint Dynamics Modeling (Year: 2022) (Year: 2022).*

(Continued)

*Primary Examiner* — Ronnie M Mancho
(74) *Attorney, Agent, or Firm* — Artegis Law Group, LLP

(57) ABSTRACT

Disturbance compensation in teleoperated devices include a first articulated arm, a second articulated arm, and a control unit. The control unit is configured to detect a first disturbance to the first articulated arm occurring at a first time, the first disturbance moving an imaging device supported by the first articulated arm away from a first orientation of the imaging device toward a second orientation of the imaging device, and after the first time: receive a first indication of a first user input to move an end effector supported by the second articulated arm while the imaging device is not at the first orientation, determine, based on the first indication, a first command for moving the end effector as if the imaging device has the first orientation, and command a second plurality of actuators of the second articulated arm to move the end effector according to the first command.

20 Claims, 11 Drawing Sheets

Related U.S. Application Data continuation of application No. 17/459,175, filed on Aug. 27, 2021, now Pat. No. 11,806,875, which is a continuation of application No. 16/275,232, filed on Feb. 13, 2019, now Pat. No. 11,130,231, which is a continuation of application No. 15/522,073, filed as application No. PCT/US2015/057669 on Oct. 27, 2015, now Pat. No. 10,272,569.

(60) Provisional application No. 62/134,212, filed on Mar. 17, 2015, provisional application No. 62/069,245, filed on Oct. 27, 2014.

(51) Int. Cl.
*B25J 9/06* (2006.01)
*B25J 9/16* (2006.01)
*B25J 19/00* (2006.01)
*B25J 19/02* (2006.01)
*A61B 34/20* (2016.01)
*A61B 34/35* (2016.01)
*A61B 90/00* (2016.01)
*A61B 90/50* (2016.01)

(52) U.S. Cl.
CPC ........... *B25J 9/1653* (2013.01); *B25J 9/1682* (2013.01); *B25J 19/0004* (2013.01); *B25J 19/021* (2013.01); *A61B 2034/2059* (2016.02); *A61B 2034/305* (2016.02); *A61B 34/35* (2016.02); *A61B 90/361* (2016.02); *A61B 2090/373* (2016.02); *A61B 2090/508* (2016.02); *Y10S 901/02* (2013.01)

(58) Field of Classification Search
CPC ........ B25J 19/021; A61B 34/30; A61B 34/35; A61B 90/361; A61B 2034/2059; A61B 2034/305; A61B 2090/373; A61B 2090/508; A61B 34/20; A61B 34/70; A61B 90/50; Y10S 901/02
USPC .......................................................... 700/251
See application file for complete search history.

(56) References Cited

U.S. PATENT DOCUMENTS 4,640,663 A 2/1987 Niinomi et al.
4,693,665 A 9/1987 Friederichs et al.
4,815,006 A 3/1989 Andersson et al.
4,894,855 A 1/1990 Kresse
4,928,047 A 5/1990 Arai et al.
4,945,914 A 8/1990 Allen
5,144,213 A 9/1992 Sasaki et al.
5,222,499 A 6/1993 Allen et al.
5,397,323 A 3/1995 Taylor et al.
5,402,801 A 4/1995 Taylor
5,657,429 A 8/1997 Wang et al.
5,784,542 A 7/1998 Ohm et al.
5,790,307 A 8/1998 Mick et al.
5,876,325 A 3/1999 Mizuno et al.
5,994,864 A 11/1999 Inoue et al.
6,035,228 A 3/2000 Yanof et al.
6,120,433 A 9/2000 Mizuno et al.
6,146,200 A 11/2000 Ito et al.
6,200,024 B1 * 3/2001 Negrelli ............... A61B 6/4476 378/197
6,246,200 B1 6/2001 Blumenkranz et al.
6,424,885 B1 7/2002 Niemeyer et al.
6,471,165 B2 10/2002 Twisselmann
6,471,167 B1 10/2002 Myers et al.
6,560,492 B2 5/2003 Borders
6,565,554 B1 5/2003 Niemeyer
6,788,018 B1 9/2004 Blumenkranz
7,074,179 B2 7/2006 Wang et al.
7,089,612 B2 8/2006 Rocher et al.
7,155,315 B2 12/2006 Niemeyer et al.
7,155,316 B2 12/2006 Sutherland et al.
7,189,246 B2 3/2007 Otsuka et al.
7,720,322 B2 5/2010 Prisco et al.
7,725,214 B2 * 5/2010 Diolaiti ................ A61B 1/0016 606/1
7,741,802 B2 6/2010 Prisco et al.
7,763,015 B2 7/2010 Cooper et al.
7,837,674 B2 11/2010 Cooper
7,852,030 B2 12/2010 Kamiya
8,004,229 B2 8/2011 Nowlin et al.
8,041,459 B2 10/2011 Sutherland et al.
8,062,211 B2 * 11/2011 Duval ................ A61B 1/00087 600/114
8,069,714 B2 12/2011 Ortmaier et al.
8,083,667 B2 * 12/2011 Cooper ............. A61B 1/00154 600/106
8,170,717 B2 5/2012 Sutherland et al.
8,182,415 B2 * 5/2012 Larkin ................... A61B 34/71 901/14
8,226,072 B2 7/2012 Murayama
8,271,130 B2 9/2012 Hourtash et al.
8,287,522 B2 * 10/2012 Moses .................... A61B 34/76 606/1
8,377,046 B2 * 2/2013 Cooper .................. A61B 1/002 606/1
8,396,598 B2 3/2013 Sutherland et al.
8,400,094 B2 3/2013 Schena
8,457,279 B2 * 6/2013 Saracen ............... A61B 6/0487 378/68
8,464,720 B1 6/2013 Pigazzi et al.
8,541,970 B2 9/2013 Nowlin et al.
8,548,629 B2 * 10/2013 Ortmaier .............. A61B 6/4458 378/197
8,551,076 B2 * 10/2013 Duval ................ A61B 1/00183 606/1
8,620,473 B2 12/2013 Diolaiti et al.
8,621,954 B1 1/2014 Dellon et al.
8,624,537 B2 1/2014 Nowlin et al.
8,641,621 B2 2/2014 Razzaque et al.
8,672,833 B2 * 3/2014 Cooper ............. A61B 1/00193 606/1
8,679,099 B2 * 3/2014 Cooper .................. A61B 34/32 606/1
8,740,885 B2 * 6/2014 Larkin ................... A61B 34/71 606/1
8,749,189 B2 6/2014 Nowlin et al.
8,749,190 B2 6/2014 Nowlin et al.
8,786,241 B2 7/2014 Nowlin et al.
8,816,628 B2 8/2014 Nowlin et al.
8,823,308 B2 9/2014 Nowlin et al.
8,852,208 B2 10/2014 Gomez et al.
8,911,499 B2 12/2014 Quaid et al.
8,918,211 B2 12/2014 Diolaiti et al.
9,060,678 B2 6/2015 Larkin et al.
9,078,686 B2 7/2015 Schena
9,084,623 B2 7/2015 Gomez et al.
9,102,058 B2 8/2015 Hofmann et al.
9,107,633 B2 * 8/2015 Muller ................. A61B 6/4458
9,107,683 B2 8/2015 Houtash et al.
9,138,129 B2 9/2015 Diolaiti
9,195,412 B2 11/2015 Brown et al.
9,220,567 B2 12/2015 Sutherland et al.
9,295,524 B2 3/2016 Schena et al.
9,296,104 B2 3/2016 Swarup et al.
9,333,042 B2 5/2016 Diolaiti et al.
9,334,911 B2 5/2016 Kameta et al.
9,345,544 B2 5/2016 Hourtash et al.
9,375,284 B2 6/2016 Hourtash
9,387,593 B2 7/2016 Bonin et al.
9,415,510 B2 8/2016 Hourtash et al.
9,468,501 B2 10/2016 Hourtash et al.
9,469,034 B2 10/2016 Diolaiti et al.
9,492,235 B2 11/2016 Hourtash et al.
9,492,927 B2 11/2016 Diolaiti et al.
9,615,728 B2 4/2017 Charles et al.
9,642,606 B2 5/2017 Charles et al.

(56) References Cited

U.S. PATENT DOCUMENTS 9,788,909 B2 10/2017 Larkin et al.
9,918,681 B2 3/2018 Wallace et al.
9,949,620 B2 * 4/2018 Duval .................. A61B 1/0051
10,028,793 B2 7/2018 Griffiths et al.
10,034,717 B2 7/2018 Miller et al.
10,039,473 B2 8/2018 Zhao et al.
10,064,689 B2 9/2018 Swarup et al.
10,226,306 B2 3/2019 Itkowitz et al.
10,231,790 B2 3/2019 Quaid et al.
10,258,414 B2 4/2019 O'Grady et al.
10,258,419 B2 4/2019 Auld et al.
10,272,569 B2 4/2019 Swarup et al.
10,376,324 B2 8/2019 Kerdok et al.
10,405,944 B2 9/2019 Swarup et al.
10,485,617 B2 11/2019 Crawford et al.
10,555,777 B2 2/2020 Griffiths et al.
10,603,135 B2 3/2020 Azizian et al.
10,617,479 B2 4/2020 Itkowitz et al.
10,624,807 B2 4/2020 Itkowitz et al.
10,682,190 B2 6/2020 Griffiths et al.
10,905,500 B2 2/2021 Griffiths et al.
10,993,772 B2 5/2021 Itkowitz et al.
11,130,231 B2 9/2021 Swarup et al.
11,173,005 B2 11/2021 Azizian et al.
11,179,221 B2 11/2021 Swarup et al.
11,413,103 B2 8/2022 Griffiths et al.
11,419,687 B2 8/2022 Itkowitz et al.
11,426,245 B2 8/2022 Quaid et al.
11,576,737 B2 2/2023 Itkowitz et al.
11,672,618 B2 6/2023 Itkowitz et al.
11,684,448 B2 6/2023 Swarup et al.
11,737,842 B2 8/2023 Griffiths et al.
11,759,265 B2 9/2023 Griffiths et al.
11,806,875 B2 11/2023 Swarup et al.
11,896,326 B2 2/2024 Itkowitz et al.
12,024,528 B2 7/2024 Chu et al.
12,035,987 B2 7/2024 Itkowitz et al.
12,064,201 B2 8/2024 Griffiths et al.
12,179,359 B2 12/2024 Swarup et al.
12,186,033 B2 * 1/2025 Griffiths ................. A61G 13/04
12,232,834 B2 2/2025 Itkowitz et al.
2001/0013764 A1 8/2001 Blumenkranz et al.
2002/0082612 A1 6/2002 Moll et al.
2002/0161446 A1 10/2002 Bryan et al.
2003/0192758 A1 10/2003 Murata et al.
2006/0025668 A1 2/2006 Peterson et al.
2006/0101581 A1 5/2006 Blanchard et al.
2006/0149418 A1 7/2006 Anvari
2007/0096670 A1 5/2007 Hashimoto et al.
2007/0185376 A1 8/2007 Wilson et al.
2007/0270685 A1 11/2007 Kang et al.
2007/0287992 A1 12/2007 Diolaiti et al.
2008/0004633 A1 1/2008 Arata et al.
2008/0046122 A1 2/2008 Manzo et al.
2008/0064921 A1 3/2008 Larkin et al.
2008/0065108 A1 3/2008 Diolaiti
2008/0071288 A1 * 3/2008 Larkin ..................... A61B 1/06
901/14
2008/0125649 A1 5/2008 Meyer et al.
2008/0312529 A1 12/2008 Amiot et al.
2009/0000136 A1 1/2009 Crampton
2009/0024142 A1 1/2009 Ruiz Morales
2009/0088774 A1 4/2009 Swarup et al.
2009/0209976 A1 8/2009 Rosielle
2009/0216372 A1 8/2009 Watanabe et al.
2009/0326324 A1 12/2009 Munoz et al.
2010/0042097 A1 2/2010 Newton et al.
2010/0131102 A1 5/2010 Herzog et al.
2010/0138183 A1 6/2010 Jensen et al.
2010/0168762 A1 7/2010 Osawa et al.
2010/0204713 A1 8/2010 Ruiz Morales
2010/0228249 A1 9/2010 Mohr et al.
2010/0228264 A1 9/2010 Robinson et al.
2010/0286712 A1 11/2010 Won et al.
2010/0292843 A1 11/2010 Kariyazaki et al.
2011/0015521 A1 1/2011 Faul
2011/0071508 A1 3/2011 Duval et al.
2011/0126801 A1 6/2011 Walter
2011/0276179 A1 11/2011 Banks et al.
2011/0282351 A1 11/2011 Cooper et al.
2011/0308536 A1 12/2011 Govari
2012/0022553 A1 * 1/2012 Cooper .............. A61B 1/00165
606/130
2012/0029694 A1 2/2012 Muller
2012/0071895 A1 3/2012 Stahler et al.
2012/0083654 A1 * 4/2012 Cooper .............. A61B 1/00149
600/106
2012/0101508 A1 4/2012 Wook Choi et al.
2012/0198621 A1 8/2012 Daley
2012/0203271 A1 * 8/2012 Larkin ............... A61B 1/00087
606/1
2012/0221011 A1 * 8/2012 Larkin ............... A61B 1/00149
606/108
2012/0277901 A1 11/2012 Jacobsen et al.
2013/0053868 A1 * 2/2013 Cooper .................. A61B 90/10
606/130
2013/0072822 A1 3/2013 Auchinleck et al.
2013/0085510 A1 4/2013 Stefanchik et al.
2013/0096701 A1 4/2013 Suorajaervi et al.
2013/0110129 A1 5/2013 Reid et al.
2013/0123799 A1 5/2013 Smith et al.
2013/0144116 A1 * 6/2013 Cooper ............. A61B 1/00165
600/102
2013/0152307 A1 6/2013 Bennett-Guerrero
2013/0205558 A1 8/2013 Sporer et al.
2013/0283980 A1 10/2013 Petrak et al.
2013/0327902 A1 12/2013 Frick et al.
2013/0338679 A1 12/2013 Rosielle et al.
2014/0005488 A1 1/2014 Charles et al.
2014/0005555 A1 1/2014 Tesar
2014/0005654 A1 1/2014 Batross et al.
2014/0033434 A1 2/2014 Jackson
2014/0033436 A1 2/2014 Jackson
2014/0039517 A1 2/2014 Bowling et al.
2014/0039681 A1 2/2014 Bowling et al.
2014/0052153 A1 2/2014 Griffiths et al.
2014/0052154 A1 2/2014 Griffiths et al.
2014/0055489 A1 2/2014 Itkowitz et al.
2014/0163736 A1 6/2014 Azizian et al.
2014/0206936 A1 * 7/2014 Cooper ............. A61B 1/00149
600/109
2014/0222207 A1 8/2014 Bowling et al.
2014/0276887 A1 9/2014 Stein et al.
2014/0305995 A1 10/2014 Shelton, IV et al.
2014/0316252 A1 10/2014 Kwak et al.
2014/0316430 A1 10/2014 Hourtash et al.
2014/0350387 A1 11/2014 Siewerdsen et al.
2014/0358161 A1 12/2014 Hourtash et al.
2015/0032126 A1 1/2015 Nowlin et al.
2015/0051733 A1 2/2015 Nowlin et al.
2015/0113733 A1 4/2015 Diel et al.
2015/0117601 A1 4/2015 Keeve et al.
2015/0119637 A1 4/2015 Alvarez et al.
2015/0150639 A1 6/2015 Diolaiti et al.
2015/0224845 A1 8/2015 Anderson et al.
2015/0250546 A1 * 9/2015 Larkin ................ A61B 5/0086
606/130
2016/0000512 A1 1/2016 Gombert et al.
2016/0081754 A1 3/2016 Kostrzewski et al.
2016/0098943 A1 4/2016 Valeev et al.
2016/0113728 A1 4/2016 Piron et al.
2016/0156288 A1 6/2016 Sawamura et al.
2016/0242849 A9 8/2016 Crawford et al.
2017/0079731 A1 3/2017 Griffiths et al.
2017/0143429 A1 5/2017 Richmond et al.
2017/0181806 A1 6/2017 Itkowitz et al.
2017/0265949 A1 9/2017 Crawford et al.
2018/0078320 A1 3/2018 Griffiths
2018/0338808 A1 11/2018 Swarup et al.
2018/0344421 A1 12/2018 Cagle et al.
2019/0183593 A1 6/2019 Hourtash et al.
2019/0192233 A1 6/2019 O'Grady et al.
2019/0216550 A1 7/2019 Eyre et al.

(56) References Cited

U.S. PATENT DOCUMENTS

| | | | |
|---|---|---|---|
| 2019/0216555 | A1 | 7/2019 | DiMaio et al. |
| 2019/0231460 | A1 | 8/2019 | DiMaio et al. |
| 2020/0093549 | A1 | 3/2020 | Chin et al. |
| 2020/0107897 | A1 | 4/2020 | Menzies et al. |
| 2023/0372029 | A1 | 11/2023 | Griffiths et al. |
| 2024/0009837 | A1 | 1/2024 | Swarup et al. |
| 2024/0115332 | A1 | 4/2024 | Itkowitz et al. |
| 2024/0315786 | A1 | 9/2024 | Itkowitz et al. |
| 2024/0358462 | A1 | 10/2024 | Griffiths et al. |
| 2025/0090243 | A1 | 3/2025 | Griffiths et al. |
| 2025/0143815 | A1 | 5/2025 | Itkowitz et al. |
| 2025/0359952 | A1 | 11/2025 | Itkowitz et al. |
| 2025/0359954 | A1 | 11/2025 | Griffiths et al. |

FOREIGN PATENT DOCUMENTS

| | | | |
|---|---|---|---|
| CN | 2910169 | Y | 6/2007 |
| CN | 101049248 | A | 10/2007 |
| CN | 101049697 | A | 10/2007 |
| CN | 101064060 | A | 10/2007 |
| CN | 101160104 | A | 4/2008 |
| CN | 101217913 | A | 7/2008 |
| CN | 101222889 | A | 7/2008 |
| CN | 201082167 | Y | 7/2008 |
| CN | 101314224 | A | 12/2008 |
| CN | 101332137 | A | 12/2008 |
| CN | 101449292 | A | 6/2009 |
| CN | 101466342 | A | 6/2009 |
| CN | 101472546 | A | 7/2009 |
| CN | 101720269 | A | 6/2010 |
| CN | 101827735 | A | 9/2010 |
| CN | 101959656 | A | 1/2011 |
| CN | 102046336 | A | 5/2011 |
| CN | 102046360 | A | 5/2011 |
| CN | 101443163 | B | 8/2011 |
| CN | 102389334 | A | 3/2012 |
| CN | 102429726 | A | 5/2012 |
| CN | 101234033 | B | 6/2012 |
| CN | 102715924 | A | 10/2012 |
| CN | 102727312 | A | 10/2012 |
| CN | 102727358 | A | 10/2012 |
| CN | 103027818 | A | 4/2013 |
| CN | 103221015 | A | 7/2013 |
| CN | 103315818 | A | 9/2013 |
| CN | 103637895 | A | 3/2014 |
| CN | 103720514 | A | 4/2014 |
| CN | 103889663 | A | 6/2014 |
| CN | 104039629 | A | 9/2014 |
| CN | 104002296 | B | 5/2016 |
| DE | 3119577 | A1 | 12/1982 |
| DE | 10249786 | A1 | 5/2004 |
| DE | 202014000027 | U1 | 1/2014 |
| DE | 102010038800 | B4 | 3/2024 |
| EP | 1915963 | A1 | 4/2008 |
| EP | 1974870 | A1 | 10/2008 |
| EP | 2047805 | A1 | 4/2009 |
| EP | 2332477 | A2 | 6/2011 |
| EP | 2332479 | A2 | 6/2011 |
| EP | 2332482 | A2 | 6/2011 |
| EP | 2581073 | A1 | 4/2013 |
| EP | 2735278 | A2 | 5/2014 |
| EP | 2023843 | B1 | 3/2016 |
| JP | H0355182 | A | 3/1991 |
| JP | H05138583 | A | 6/1993 |
| JP | H06278063 | A | 10/1994 |
| JP | H07185817 | A | 7/1995 |
| JP | H07328016 | A | 12/1995 |
| JP | H0884735 | A | 4/1996 |
| JP | H09254079 | A | 9/1997 |
| JP | H09300264 | A | 11/1997 |
| JP | H10100085 | A | 4/1998 |
| JP | H11226062 | A | 8/1999 |
| JP | 2000107200 | A | 4/2000 |
| JP | 2000300579 | A | 10/2000 |
| JP | 2002307344 | A | 10/2002 |
| JP | 2002345831 | A | 12/2002 |
| JP | 2003131701 | A | 5/2003 |
| JP | 2003299674 | A | 10/2003 |
| JP | 2004216022 | A | 8/2004 |
| JP | 2004223128 | A | 8/2004 |
| JP | 2004358239 | A | 12/2004 |
| JP | 2004538037 | A | 12/2004 |
| JP | 2006263894 | A | 10/2006 |
| JP | 2008259607 | A | 10/2008 |
| JP | 2008538301 | A | 10/2008 |
| JP | 2010194101 | A | 9/2010 |
| JP | 2011212837 | A | 10/2011 |
| JP | 2012005557 | A | 1/2012 |
| JP | 2012239709 | A | 12/2012 |
| JP | 2013252427 | A | 12/2013 |
| JP | 2015502768 | A | 1/2015 |
| KR | 20060135063 | A | 12/2006 |
| KR | 20100067846 | A | 6/2010 |
| WO | WO-9403113 | A1 | 2/1994 |
| WO | WO-2006039092 | A2 | 4/2006 |
| WO | WO-2006069288 | A2 | 6/2006 |
| WO | WO-2006079108 | A1 | 7/2006 |
| WO | WO-2006124390 | A2 | 11/2006 |
| WO | WO-2007136768 | A2 | 11/2007 |
| WO | WO-2007136770 | A2 | 11/2007 |
| WO | WO-2008002830 | A2 | 1/2008 |
| WO | WO-2010068005 | A2 | 6/2010 |
| WO | WO-2011060042 | A1 | 5/2011 |
| WO | WO-2011060139 | A2 | 5/2011 |
| WO | WO-2011109041 | A1 | 9/2011 |
| WO | WO-2011143016 | A1 | 11/2011 |
| WO | WO-2011143338 | A1 | 11/2011 |
| WO | WO-2012064528 | A1 | 5/2012 |
| WO | WO-2012158458 | A2 | 11/2012 |
| WO | WO-2013048957 | A1 | 4/2013 |
| WO | WO-2013071057 | A1 | 5/2013 |
| WO | WO-2013071071 | A1 | 5/2013 |
| WO | WO-2013181503 | A1 | 12/2013 |
| WO | WO-2013181507 | A1 | 12/2013 |
| WO | WO-2013181516 | A1 | 12/2013 |
| WO | WO-2014028703 | A1 | 2/2014 |
| WO | WO-2014146095 | A1 | 9/2014 |
| WO | WO-2014146107 | A1 | 9/2014 |
| WO | WO-2014146113 | A1 | 9/2014 |
| WO | WO-2014146119 | A1 | 9/2014 |
| WO | WO-2014146120 | A1 | 9/2014 |
| WO | WO-2015142798 | A1 | 9/2015 |
| WO | WO-2015142930 | A1 | 9/2015 |
| WO | WO-2015142943 | A1 | 9/2015 |
| WO | WO-2015142947 | A1 | 9/2015 |
| WO | WO-2016069648 | A1 | 5/2016 |
| WO | WO-2016069655 | A1 | 5/2016 |
| WO | WO-2016069659 | A1 | 5/2016 |
| WO | WO-2016069660 | A1 | 5/2016 |
| WO | WO-2016069661 | A1 | 5/2016 |
| WO | WO-2016069663 | A1 | 5/2016 |
| WO | WO-2020257565 | A1 | 12/2020 |

OTHER PUBLICATIONS

Extended European Search Report for Application No. EP25198848.1, mailed on Dec. 2, 2025, 6 pages.
Extended European Search Report for Application No. EP25162399.7, mailed on Jun. 26, 2025. 10 pages.
Extended European Search Report for Application No. EP25186077.1, mailed on Oct. 6, 2025, 10 pages.
Extended European Search Report for Application No. 15855456.8, mailed on Sep. 25, 2018, 10 pages.
Extended European Search Report for Application No. EP15854136.7, mailed on Jun. 7, 2018, 11 pages.
Extended European Search Report for Application No. EP15854253, mailed on May 11, 2018, 11 pages.
Extended European Search Report for Application No. EP15854260.5, mailed on Jun. 7, 2018, 8 pages.
Extended European Search Report for Application No. EP15855051.7, mailed on May 3, 2018, 10 pages.
Extended European Search Report for Application No. EP15855097, mailed on Apr. 25, 2018, 11 pages.

(56) References Cited

OTHER PUBLICATIONS

Extended European Search Report for Application No. EP15855351.1, mailed on Apr. 30, 2018, 9 pages.
Extended European Search Report for Application No. EP20182993.4, mailed on Oct. 2, 2020, 13 pages.
Extended European Search Report for Application No. EP22178252, mailed on Sep. 30, 2022, 07 pages.
Extended European Search Report for European Application No. 21181826.5 dated Oct. 26, 2021, 8 pages.
Fresenius.. "A Robot at the Operating Table." 2019, 06 Pages.
International Search Report and Written Opinion for Application No. PCT/US2015/057656, mailed on Feb. 1, 2016, 11 pages.
International Search Report and Written Opinion for Application No. PCT/US2015/057658, mailed on Feb. 1, 2016, 12 pages.
International Search Report and Written Opinion for Application No. PCT/US2015/057664, mailed on Feb. 1, 2016, 8 pages.
International Search Report and Written Opinion for Application No. PCT/US2015/057669, mailed on Feb. 1, 2016, 9 pages.
International Search Report and Written Opinion for Application No. PCT/US2015/057670, mailed on Feb. 1, 2016, 8 pages.
International Search Report and Written Opinion for Application No. PCT/US2015/057671, mailed on Feb. 1, 2016, 6 pages.
International Search Report and Written Opinion for Application No. PCT/US2015/057673, mailed on Feb. 1, 2016, 10 pages.
Li J., et al., "Vibration Prediction of the Robotic Arm Based on Elastic Joint Dynamics Modeling," Sensors, Aug. 2022, vol. 22(16), pp. 1-20.
Ma Y, and Li Y. Active Disturbance Compensation Based Robust Control for Speed Regulation System of Permanent Magnet Synchronous Motor, Applied Sciences, (Year: 2019), pp. 1-13.
Macrae M., "The Robo-Doctor Will See You Now," Medical Equipment and Device Manufacturing, Robotics, The American Society of Mechanical Engineers, May 2012, 8 Pages.
Office Action for Chinese Application No. CN202010672351, mailed Nov. 28, 2023. 29 pages.
Partial Supplementary European Search Report for Application No. EP15855456.8, mailed on May 23, 2018, 11 pages.
U.S. Appl. No. 61/954,120, inventor Hourtash; Arjang M., filed Mar. 17, 2014.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Wang Y,, et al., "Disturbance Compensation based Controller for an Indoor Blimp Robot," Robotics and Autonomous Systems, (Year: 2020), pp. 1-15.
Extended European Search Report for Application No. EP24210151.7, mailed on May 7, 2025, 11 pages.

* cited by examiner

DISTURBANCE COMPENSATION IN COMPUTER-ASSISTED DEVICES

CROSS REFERENCE TO RELATED APPLICATIONS

This application is a continuation of U.S. patent application Ser. No. 18/474,388 (filed on Sep. 26, 2023), which a continuation of U.S. patent application Ser. No. 17/459,175 (filed on Aug. 27, 2021 and issued as U.S. Pat. No. 11,806, 875), which is a continuation of U.S. patent application Ser. No. 16/275,232 (filed on Feb. 13, 2019 and issued as U.S. Pat. No. 11,130,231), which is a continuation of U.S. patent application Ser. No. 15/522,073 (filed on Apr. 26, 2017 and issued as U.S. Pat. No. 10,272,569), which is a U.S. National Stage patent application of International Patent Application No. PCT/US2015/057669 (filed on Oct. 27 2015), the benefit of which is claimed, and claims priority to U.S. Provisional Patent Application No. 62/134,212 entitled "System and Method for Reducing Tool Disturbances," which was filed Mar. 17, 2015, and U.S. Provisional Patent Application No. 62/069,245 entitled "System and Method for Integrated Operating Table," which was filed Oct. 27, 2014. The subject matter of these related applications is hereby incorporated herein by reference.

TECHNICAL FIELD

The present disclosure relates generally to operation of devices with articulated arms and more particularly to reducing external disturbances to an instrument pose.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more articulated arms and/or end effectors. These one or more articulated arms and/or end effectors each include a combination of links and articulated joints that support motion of the articulated arms and/or end effectors. In many cases, the articulated joints are manipulated to obtain a desired position and/or orientation (collectively, a desired pose) of a corresponding instrument located at a distal end of the links and articulated joints of a corresponding articulated arm and/or end effector. Each of the articulated joints proximal to the instrument provides the corresponding articulated arm and/or end effector with at least one degree of freedom that may be used to manipulate the position and/or orientation of the corresponding instrument. In many cases, the corresponding articulated arms and/or end effectors may include at least six degrees of freedom that allow for controlling a x, y, and z position (collectively referred to as translational movement) of the corresponding instrument as well as a roll, pitch, and yaw orientation (collectively referred to as rotational movement) of the corresponding instrument. To provide for greater flexibility in control of the pose of the corresponding instrument, the corresponding articulated arms and/or end effectors are often designed to include redundant degrees of freedom. When redundant degrees of freedom are present it is possible that multiple different combinations of positions and/or orientations of the articulated joints may be used to obtain the same pose of the corresponding instrument.

When devices with articulated arms are used for a medical procedure, it is not uncommon that one or more of the articulated arms may be docked with a patient at a port site so that an instrument and/or other end effector may be utilized to perform a procedure on the interior anatomy of the patient. Depending upon the procedure it may be desirable to release a lock and/or brake on one or more of the joints of the articulated arm in order to reposition at least a portion of the articulated arm. When the lock and/or brake is released, this may result in an undesirable movement in the position and/or orientation of the articulated arm and more importantly a tip of the instrument and/or end effector that is positioned within the patient. This undesirable movement may result in injury to a patient, injury to personnel in proximity to the articulated arms and/or end effectors, damage to the articulated arms and/or end effectors, damage to other devices in proximity to the articulated arms and/or end effectors, breach of a sterile field, and/or other undesirable outcomes.

Accordingly, it would be desirable to have the one or more joints in an articulated arm correct for undesirable movement in an instrument, an articulated arm, and/or an end effector when a brake and/or a lock is released in one or more joints of the articulated arm.

SUMMARY

Consistent with some embodiments, a computer-assisted medical device includes a first joint set on an articulated arm, a second joint set on the articulated arm, and a control unit coupled to the first joint set and second joint set. In some embodiments, the control unit is configured to determine a disturbance to the first joint set caused by a release of one or more brakes and compensate for the disturbance using the second joint set to reduce motion to a position of a point of interest.

Consistent with some embodiments, a method of controlling motion in a medical device includes determining a first saved transform, the first saved transform being a transform between two coordinate frames spanning a first joint set of an articulated arm of the medical device before a disturbance; determining a second saved transform, the second saved transform being a transform between two coordinate frames spanning a second joint set of the articulated arm; receiving the disturbance, the disturbance disturbing the position of one or more joints in the first joint set; determining a third transform, the third transform being a transform between two coordinate frames spanning the first joint set after the disturbance; and determining a predicted motion of a point of interest caused by the disturbance. In some examples, predicted motion of a point of interest caused by the disturbance includes calculating a difference between a first positional determination based on the first and second saved transform and a second positional determination based on the third transform and second saved transform.

Consistent with some embodiments, a method of controlling motion in a medical device includes determining a first saved transform, the first saved transform being a transform between two coordinate frames spanning a first joint set of an articulated arm of the medical device before a disturbance; determining a second saved transform, the second saved transform being a transform between two coordinate frames spanning a second joint set of the articulated arm; receiving the disturbance, the disturbance disturbing the position of one or more joints in the first joint set; determining a third transform, the third transform being a transform between two coordinate frames spanning the first joint set after the disturbance; and determining a predicted motion of a point of interest caused by the disturbance. In some examples, determining a predicted motion of a point of interest caused by the disturbance includes calculating a difference between a first positional determination based on the first and second saved transform and a second positional determination based on the third transform and second saved transform.

Consistent with some embodiments, a computer-assisted medical device includes a first articulated arm with an imaging device, a second articulated arm with an end effector, a control unit coupled to the first articulated arm and second articulated arm. In some examples the control unit is configured to set a first reference frame, the first reference frame being based on the position of the imaging device at a first time, allow a first disturbance to the first articulated arm moving the imaging device away from the position of the imaging device at the first time, receive commands to move the end effector, and transform the commands to move the end effector from the first reference frame to commands to move the end effector in a reference frame for the end effector.

Consistent with some embodiments, a non-transitory machine-readable medium comprising a plurality of machine-readable instructions which when executed by one or more processors associated with a medical device are adapted to cause the one or more processors to perform a method including determining a first saved transform, the first saved transform being a transform between two coordinate frames spanning a first joint set of an articulated arm of the medical device before a disturbance; determining a second saved transform, the second saved transform being a transform between two coordinate frames spanning a second joint set of the articulated arm; receiving the disturbance, the disturbance disturbing the position of one or more joints in the first joint set; determining a third transform, the third transform being a transform between two coordinate frames spanning the first joint set after the disturbance; and determining a predicted motion of a point of interest caused by the disturbance. In some examples, determining a predicted motion on a point of interest caused by the disturbance includes calculating a difference between a first positional determination based on the first and second saved transform and a second positional determination based on the third transform and second saved transform.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. The term "including" means including but not limited to, and each of the one or more individual items included should be considered optional unless otherwise stated. Similarly, the term "may" indicates that an item is optional.

Figure 1:
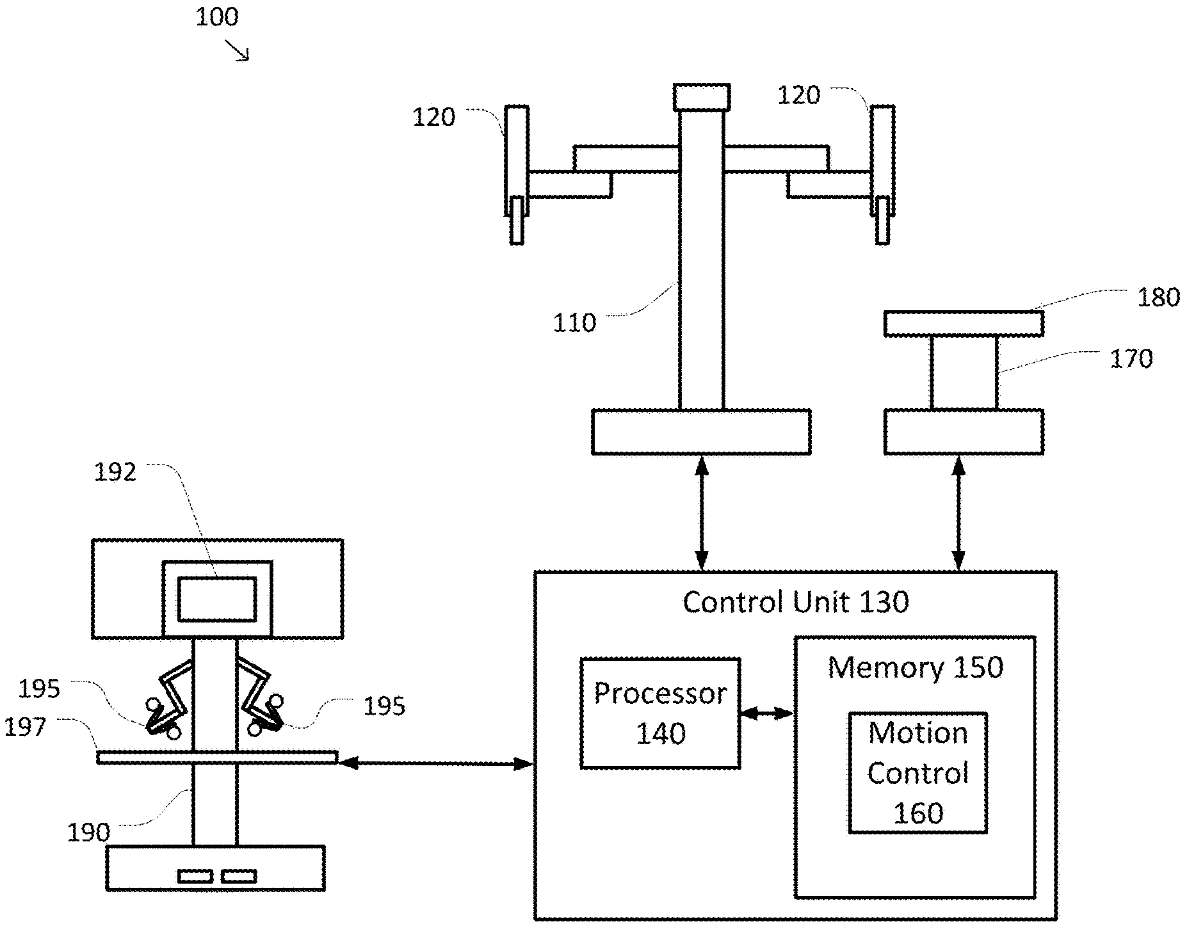
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a device 110 with one or more movable or articulated arms 120. Each of the one or more articulated arms 120 supports one or more end effectors. In some examples, device 110 may be consistent with a computer-assisted surgical device. The one or more articulated arms 120 each provides support for one or more instruments, surgical instruments, imaging devices, and/or the like mounted to a distal end of at least one of the articulated arms 120. In some embodiments, device 110 and the operator workstation may correspond to a da Vinci® Surgical System commercialized by Intuitive Surgical, Inc. of Sunnyvale, California. In some embodiments, computer-assisted surgical devices with other configurations, fewer or more articulated arms, and/or the like may optionally be used with computer-assisted system 100.

Device 110 is coupled to a control unit 130 via an interface. The interface may include one or more wireless links, cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine. In some embodiments, control unit may be included as part of the operator workstation and/or operated separately from, but in coordination with the operator workstation. Some examples of control units, such as control unit 130 may include non-transient, tangible, machine readable media that include executable code that when run by one or more processors (e.g., processor 140) may cause the one or more processors to perform the processes of method 400.

Memory 150 is used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that supports autonomous and/or semiautonomous control of device 110. Motion control application 160 may include one or more application programming interfaces (APIs) for receiving position, motion, and/or other sensor information from device 110, exchanging position, motion, and/or collision avoidance information with other control units regarding other devices, such as a surgical table and/or imaging device, and/or planning and/or assisting in the planning of motion for device 110, articulated arms 120, and/or the end effectors of device 110. And although motion control application 160 is depicted as a software application, motion control application 160 may be implemented using hardware, software, and/or a combination of hardware and software.

In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms and/or end effectors.

Computer-assisted system 100 further includes a surgical table 170. Like the one or more articulated arms 120, surgical table 170 supports articulated movement of a table top 180 relative to a base of surgical table 170. In some examples, the articulated movement of table top 180 may include support for changing a height, a tilt, a slide, a Trendelenburg orientation, and/or the like of table top 180. Although not shown, surgical table 170 may include one or more control inputs, such as a surgical table command unit for controlling the position and/or orientation of table top 180. In some embodiments, surgical table 170 may correspond to one or more of the surgical tables commercialized by Trumpf Medical Systems GmbH of Germany.

Surgical table 170 is also coupled to control unit 130 via a corresponding interface. The interface may include one or more wireless links, cables, connectors, and/or buses and may further include one or more networks with one or more network switching and/or routing devices. In some embodiments, surgical table 170 may be coupled to a different control unit than control unit 130. In some examples, motion control application 160 may include one or more application programming interfaces (APIs) for receiving position, motion, and/or other sensor information associated with surgical table 170 and/or table top 180. In some examples, motion control application 160 may contribute to motion plans associated with collision avoidance, adapting to and/or avoid range of motion limits in joints and links, movement of articulated arms, instruments, end effectors, surgical table components, and/or the like to compensate for other motion in the articulated arms, instruments, end effectors, surgical table components, and/or the like, adjust a viewing device such as an endoscope to maintain and/or place an area of interest and/or one or more instruments or end effectors within a field of view of the viewing device. In some examples, motion control application 160 may plan and/or assist in the planning of motion for surgical table 170 and/or table top 180. In some examples, motion control application 160 may prevent motion of surgical table 170 and/or table top 180, such as by preventing movement of surgical table 170 and/or table top 180 through use of the surgical table command unit. In some examples, motion control application 160 may help register device 110 with surgical table 170 so that a geometric relationship between device 110 and surgical table 170 is known. In some examples, the geometric relationship may include a translation and/or one or more rotations between coordinate frames maintained for device 110 and surgical table 170.

Control unit 130 may further be coupled to an operator workstation 190 via the interface. Operator workstation 190 may be used by an operator, such as a surgeon, to control the movement and/or operation of the articulated arms 120 and the end effectors. To support operation of the articulated arms 120 and the end effectors, operator workstation 190 includes a display system 192 for displaying images of at least portions of one or more of the articulated arms 120 and/or end effectors. For example, display system 192 may be used when it is impractical and/or impossible for the operator to see the articulated arms 120 and/or the end effectors as they are being used. In some embodiments, display system 192 displays a video image from a video capturing device, such as an endoscope, which is controlled by one of the articulated arms 120, or a third articulated arm (not shown).

Operator workstation 190 includes a console workspace with one or more input controls 195 or master controls 195 that may be used for operating the device 110, the articulated arms 120, and/or the end effectors mounted on the articulated arms 120. Each of the input controls 195 may be coupled to the distal end of their own articulated arms so that movements of the input controls 195 are detected by the operator workstation 190 and communicated to control unit 130. To provide improved ergonomics, the console workspace may also include one or more rests, such as an arm rest 197 on which operators may rest their arms while manipulating the input controls 195. In some examples, the display system 192 and the input controls 195 may be used by the operator to teleoperate the articulated arms 120 and/or the end effectors mounted on the articulated arms 120. In some embodiments, device 110, operator workstation 190, and control unit 130 may correspond to a da Vinci® Surgical System commercialized by Intuitive Surgical, Inc. of Sunnyvale, California.

In some embodiments, other configurations and/or architectures may be used with computer-assisted system 100. In some examples, control unit 130 may be included as part of operator workstation 190 and/or device 110. In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms 120 and/or end effectors. Additionally, there may be additional workstations 190 to control additional arms that may be attached to device 110. Additionally, in some embodiments, workstation 190 may have controls for controlling surgical table 170.

Figure 2:
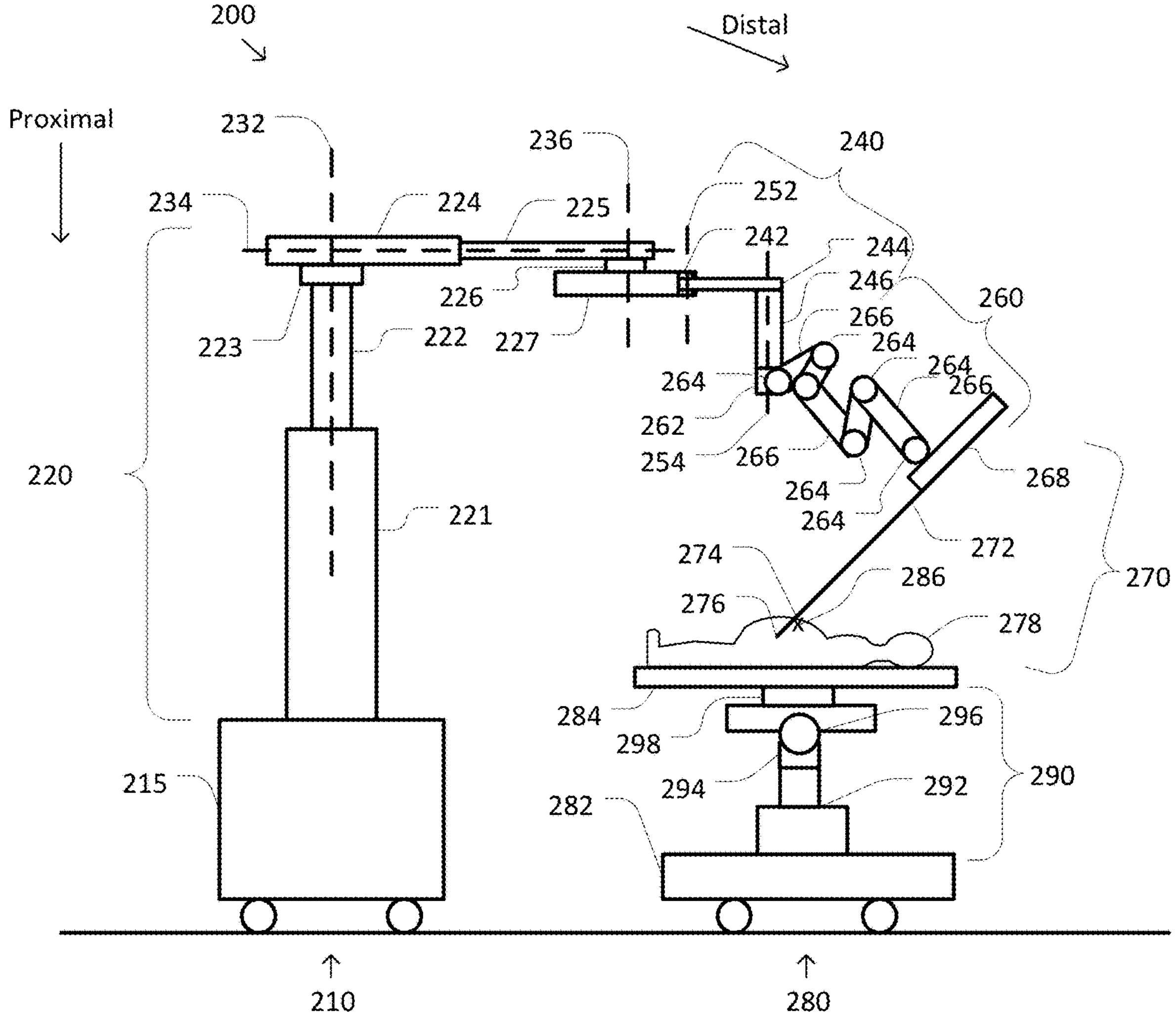
FIG. 2 is a simplified diagram showing a computer-assisted system according to some embodiments.

FIG. 2 is a simplified diagram showing a computer-assisted system 200 according to some embodiments. For example, the computer-assisted system 200 may be consistent with computer-assisted system 100. As shown in FIG. 2, the computer-assisted system 200 includes a computer-assisted device 210 with one or more articulated arms and a surgical table 280. Although not shown in FIG. 2, the computer-assisted device 210 and the surgical table 280 are coupled together using one or more interfaces and one or more control units so that at least kinematic information about the surgical table 280 is known to the motion control application being used to perform motion of the articulated arms of the computer-assisted device 210.

The computer-assisted device 210 includes various links and joints. In the embodiments of FIG. 2, the computer-assisted device is generally divided into three different sets of links and joints. Starting at the proximal end with a mobile cart 215 or patient-side cart 215 is a set-up structure 220. Coupled to a distal end of the set-up structure is a series of links and set-up joints 240 forming an articulated arm. And coupled to a distal end of the set-up joints 240 is a multi-jointed manipulator 260. In some examples, the series of set-up joints 240 and manipulator 260 may correspond to one of the articulated arms 120. And although the computer-assisted device is shown with only one series of set-up joints 240 and a corresponding manipulator 260, one of ordinary skill would understand that the computer-assisted device may include more than one series of set-up joints 240 and corresponding manipulators 260 so that the computer-assisted device is equipped with multiple articulated arms.

As shown, the computer-assisted device 210 is mounted on the mobile cart 215. The mobile cart 215 enables the computer-assisted device 210 to be transported from location to location, such as between operating rooms or within an operating room to better position the computer-assisted device in proximity to the surgical table 280. The set-up structure 220 is mounted on the mobile cart 215. As shown in FIG. 2, the set-up structure 220 includes a two part column including column links 221 and 222. Coupled to the upper or distal end of the column link 222 is a shoulder joint 223. Coupled to the shoulder joint 223 is a two-part boom including boom links 224 and 225. At the distal end of the boom link 225 is a wrist joint 226, and coupled to the wrist joint 226 is an arm mounting platform 227.

The links and joints of the set-up structure 220 include various degrees of freedom for changing the position and orientation (i.e., the pose) of the arm mounting platform 227. For example, the two-part column is used to adjust a height of the arm mounting platform 227 by moving the shoulder joint 223 up and down along an axis 232. The arm mounting platform 227 is additionally rotated about the mobile cart 215, the two-part column, and the axis 232 using the shoulder joint 223. The horizontal position of the arm mounting platform 227 is adjusted along an axis 234 using the two-part boom. And the orientation of the arm mounting platform 227 may also be adjusted by rotation about an arm mounting platform orientation axis 236 using the wrist joint 226. Thus, subject to the motion limits of the links and joints in the set-up structure 220, the position of the arm mounting platform 227 may be adjusted vertically above the mobile cart 215 using the two-part column. The positions of the arm mounting platform 227 may also be adjusted radially and angularly about the mobile cart 215 using the two-part boom and the shoulder joint 223, respectively. And the angular orientation of the arm mounting platform 227 may also be changed using the wrist joint 226.

The arm mounting platform 227 is used as a mounting point for one or more articulated arms. The ability to adjust the height, horizontal position, and orientation of the arm mounting platform 227 about the mobile cart 215 provides a flexible set-up structure for positioning and orienting the one or more articulated arms about a work space located near the mobile cart 215 where an operation or procedure is to take place. For example, arm mounting platform 227 may be positioned above a patient so that the various articulated arms and their corresponding manipulators and instruments have sufficient range of motion to perform a surgical procedure on the patient. FIG. 2 shows a single articulated arm coupled to the arm mounting platform 227 using a first set-up joint 242. And although only one articulated arm is shown, one of ordinary skill would understand that multiple articulated arms may be coupled to the arm mounting platform 227 using additional first set-up joints.

The first set-up joint 242 forms the set-up joints 240 section of the articulated arm that is the most proximal to the patient-side cart 215. The set-up joints 240 may further include a series of joints and links. As shown in FIG. 2, the set-up joints 240 may include links 244 and 246 coupled via one or more joints (not expressly shown). The joints and links of the set-up joints 240 include the ability to rotate the set-up joints 240 relative to the arm mounting platform 227 about an axis 252 using the first set-up joint 242, adjust a radial or horizontal distance between the first set-up joint 242 and the link 246, adjust a height of a manipulator mount 262 at the distal end of link 246 relative to arm mounting platform 227 along an axis 254, and rotate the manipulator mount 262 about axis 254. In some examples, the set-up joints 240 may further include additional joints, links, and axes permitting additional degrees of freedom for altering a pose of the manipulator mount 262 relative to the arm mounting platform 227.

The manipulator 260 is coupled to the distal end of the set-up joints 240 via the manipulator mount 262. The manipulator 260 includes additional joints 264 and links 266 with an instrument carriage 268 mounted at the distal end of the manipulator 260. An instrument 270 is mounted to the instrument carriage 268. The instrument 270 includes a shaft 272, which is aligned along an insertion axis. The shaft 272 is typically aligned so that it passes through a remote center of motion. Location of the remote center of motion 274 is typically maintained in a fixed translational relationship relative to the manipulator mount 262 so that operation of the joints 264 in the manipulator 260 result in rotations of the shaft 272 about the remote center of motion 274. Depending upon the embodiment, the fixed translational relation of the remote center of motion 274 relative to the manipulator mount 262 is maintained using physical constraints in the joints 264 and links 266 of the manipulator 260, using software constraints placed on the motions permitted for the joints 264, and/or a combination of both. Representative embodiments of computer-assisted surgical devices using remote centers of motion maintained using physical constraints in joints and links are described in U.S. patent application Ser. No. 13/906,888 entitled "Redundant Axis and Degree of Freedom for Hardware-Constrained Remote Center Robotic Manipulator," which was filed May 13, 2013, and representative embodiments of computer-assisted surgical devices using remote centers of motion maintained by software constraints are described in U.S. Pat. No. 8,004,229 entitled "Software Center and Highly Configurable Robotic Systems for Surgery and Other Uses," which was filed May 19, 2005, the specifications of which are hereby incorporated by reference in their entirety. In some examples, the remote center of motion 274 may correspond to a location of a body opening, such as an incision site or an orifice, in a patient 278. Because the remote center of motion 274 corresponds to the body opening, as the instrument 270 is used, the remote center of motion 274 remains stationary relative to the patient 278 to limit stresses on the anatomy of the patient 278 at the remote center of motion 274. In some examples, the shaft 272 may be passed through a cannula (not shown) located at the body opening. In some examples, instruments having a relatively larger shaft or guide tube outer diameter (e.g., 4-5 mm or more) may be passed through the body opening using a cannula and the cannula may optionally be omitted for instruments having a relatively smaller shaft or guide tube outer diameter (e.g., 2-3 mm or less).

At the distal end of the shaft 272 is an end effector 276. The degrees of freedom in the manipulator 260 due to the joints 264 and the links 266 may permit at least control of the roll, pitch, and yaw of the shaft 272 and/or end effector 276 relative to the manipulator mount 262. In some examples, the degrees of freedom in the manipulator 260 may further include the ability to advance and/or withdraw the shaft 272 using the instrument carriage 268 so that the end effector 276 may be advanced and/or withdrawn along the insertion axis and relative to the remote center of motion 274. In some examples, the manipulator 260 may be consistent with a manipulator for use with the da Vinci® Surgical System commercialized by Intuitive Surgical, Inc. of Sunnyvale, California. In some examples, the instrument 270 may be an imaging device such as an endoscope, a gripper, a surgical instrument such as a cautery or a scalpel, and/or the like. In some examples, the end effector 276 may include additional degrees of freedom, such as roll, pitch, yaw, grip, and/or the like that allow for additional localized manipulation of portions of the end effector 276 relative to the distal end of the shaft 272.

During a surgery or other medical procedure, the patient 278 is typically located on the surgical table 280. The surgical table 280 includes a table base 282 and a table top 284 with the table base 282 being located in proximity to mobile cart 215 so that the instrument 270 and/or end effector 276 may be manipulated by the computer-assisted device 210 while the shaft 272 of instrument 270 is inserted into the patient 278 at the body opening. The surgical table 280 further includes an articulated structure 290 that includes one or more joints or links between the table base 282 and the table top 284 so that the relative location of the table top 284, and thus the patient 278, relative to the table base 282 is controlled. In some examples, the articulated structure 290 may be configured so that the table top 284 is controlled relative to a virtually-defined table motion isocenter 286 that may be located at a point above the table top 284. In some examples, isocenter 286 may be located within the interior of the patient 278. In some examples, isocenter 286 may be collocated with the body wall of the patient at or near one of the body openings, such as a body opening site corresponding to remote center of motion 274.

As shown in FIG. 2, the articulated structure 290 includes a height adjustment joint 292 so that the table top 284 may be raised and/or lowered relative to the table base 282. The articulated structure 290 further includes joints and links to change both the tilt 294 and Trendelenburg 296 orientation of the table top 284 relative to the isocenter 286. The tilt 294 allows the table top 284 to be tilted side-to-side so that either the right or left side of the patient 278 is rotated upward relative to the other side of the patient 278 (i.e., about a longitudinal or head-to-toe axis of the table top 284). The Trendelenburg 296 allows the table top 284 to be rotated so that either the feet of the patient 278 are raised (Trendelenburg) or the head of the patient 278 is raised (reverse Trendelenburg). In some examples, either the tilt 294 and/or the Trendelenburg 296 rotations may be adjusted to generate rotations about isocenter 286. The articulated structure 290 further includes additional links and joints 298 to slide the table top 284 along the longitudinal (cranial-caudal) axis relative to the table base 282 with generally a left and/or right motion as depicted in FIG. 2.

FIGS. 8A-8G are simplified schematic views that illustrate various computer-assisted device system architectures that incorporate the integrated computer-assisted device and movable surgical table features described herein. The various illustrated system components are in accordance with the principles described herein. In these illustrations, the components are simplified for clarity, and various details such as individual links, joints, manipulators, instruments, end effectors, etc. are not shown, but they should be understood to be incorporated in the various illustrated components.

In these architectures, cannulas associated with one or more surgical instruments or clusters of instruments are not shown, and it should be understood that cannulas and other instrument guide devices optionally may be used for instruments or instrument clusters having a relatively larger shaft or guide tube outer diameter (e.g., 4-5 mm or more) and optionally may be omitted for instruments having a relatively smaller shaft or guide tube outer diameter (e.g., 2-3 mm or less).

Also, in these architectures, teleoperated manipulators should be understood to include manipulators that during surgery define a remote center of motion by using hardware constraints (e.g., fixed intersecting instrument pitch, yaw, and roll axes) or software constraints (e.g., software-constrained intersecting instrument pitch, yaw, and roll axes). A hybrid of such instrument axes of rotation may be defined (e.g., hardware-constrained roll axis and software-constrained pitch and yaw axes) are also possible. Further, some manipulators may not define and constrain any surgical instrument axes of rotation during a procedure, and some manipulators may define and constrain only one or two instrument axes of rotation during a procedure.

Figure 8A:
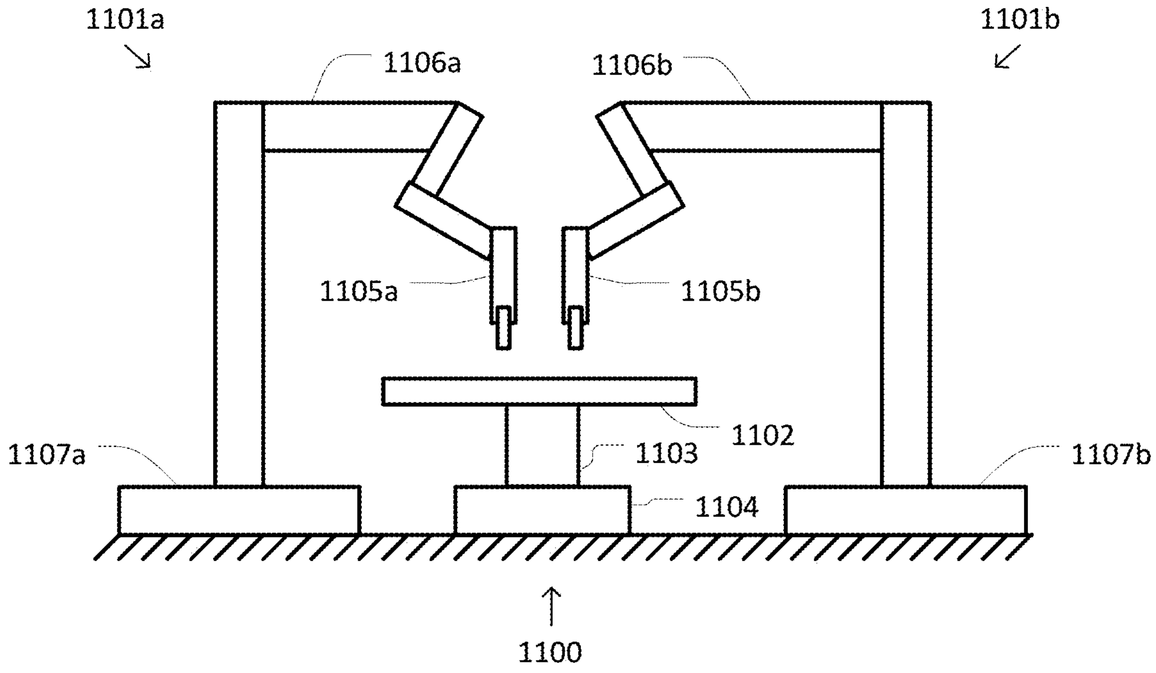
FIGS. 8A-8G are simplified schematic views that illustrate various computer-assisted device system architectures that incorporate the integrated computer-assisted device and movable surgical table features described herein.

FIG. 8A illustrates a movable surgical table 1100 and a single-instrument computer-assisted device 1101*a* are shown. Surgical table 1100 includes a movable table top 1102 and a table support structure 1103 that extends from a mechanically grounded table base 1104 to support the table top 1102 at a distal end. In some examples, surgical table 1100 may be consistent with surgical table 170 and/or 280. Computer-assisted device 1101*a* includes a teleoperated manipulator and a single instrument assembly 1105*a*. Computer-assisted device 1101*a* also includes a support structure 1106*a* that is mechanically grounded at a proximal base 1107*a* and that extends to support manipulator and instrument assembly 1105*a* at a distal end. Support structure 1106*a* is configured to allow assembly 1105*a* to be moved and held in various fixed poses with reference to surgical table 1100. Base 1107*a* is optionally permanently fixed or movable with reference to surgical table 1100. Surgical table 1100 and computer-assisted device 1101*a* operate together as described herein.

FIG. 8A further shows an optional second computer-assisted device 1101*b*, which illustrates that two, three, four, five, or more individual computer-assisted devices may be included, each having a corresponding individual teleoperated manipulator and single-instrument assembly(ies) 1105*b* supported by a corresponding support structure 1106*b*. Computer-assisted device 1101*b* is mechanically grounded, and assemblies 1105*b* are posed, similarly to computer-assisted device 1101*a*. Surgical table 1100 and computer-assisted devices 1101*a* and 1101*b* together make a multi-instrument surgical system, and they operate together as described herein. In some examples, computer-assisted devices 1101*a* and/or 1101*b* may be consistent with computer-assisted devices 110 and/or 210.

Figure 8B:
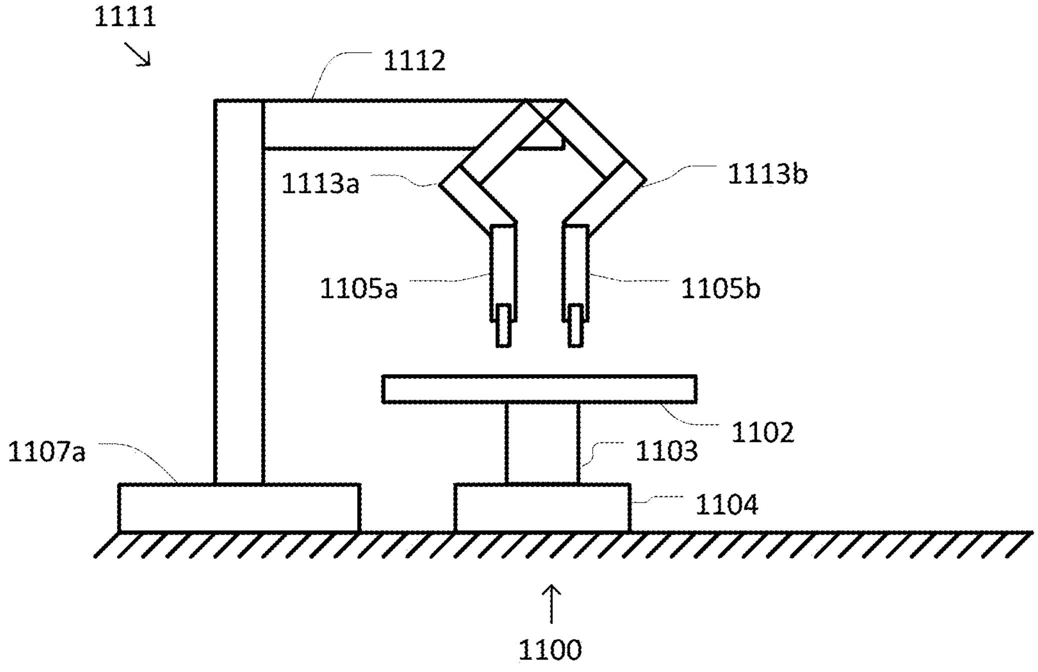

As shown in FIG. 8B, another movable surgical table 1100 and a computer-assisted device 1111 are shown. Computer-assisted device 1111 is a multi-instrument device that includes two, three, four, five, or more individual teleoperated manipulator and single-instrument assemblies as shown by representative manipulator and instrument assemblies 1105*a* and 1105*b*. The assemblies 1105*a* and 1105*b* of computer-assisted device 1111 are supported by a combined support structure 1112, which allows assemblies 1105*a* and 1105*b* to be moved and posed together as a group with reference to surgical table 1100. The assemblies 1105*a* and 1105*b* of computer-assisted device 1111 are also each supported by a corresponding individual support structure 1113*a* and 1113*b*, respectively, which allows each assembly 1105*a* and 1105*b* to be individually moved and posed with reference to surgical table 1100 and to the one or more other assemblies 1105*a* and 1105*b*. Examples of such a multi-instrument surgical system architecture are the da Vinci Si® Surgical System and the da Vinci® Xi™ Surgical System, commercialized by Intuitive Surgical, Inc. Surgical table 1100 and a surgical manipulator system including an example computer-assisted device 1111 operate together as described herein. In some examples, computer-assisted device 1111 is consistent with computer-assisted devices 110 and/or 210.

Figure 8C:
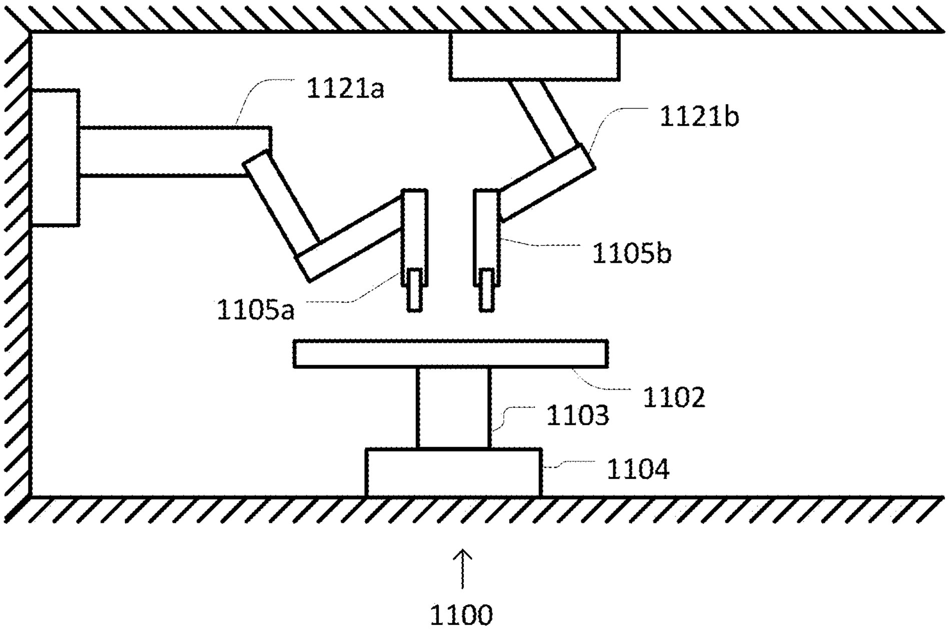

The computer-assisted devices of FIGS. 8A and 8B are each shown mechanically grounded at the floor. But, one or more such computer-assisted devices may optionally be mechanically grounded at a wall or ceiling and be permanently fixed or movable with reference to such a wall or ceiling ground. In some examples, computer-assisted devices may be mounted to the wall or ceiling using a track or grid system that allows the support base of the computer-assisted systems to be moved relative to the surgical table. In some examples, one or more fixed or releasable mounting clamps may be used to mount the respective support bases to the track or grid system. As shown in FIG. 8C, a computer-assisted device 1121*a* is mechanically grounded at a wall, and a computer-assisted device 1121*b* is mechanically grounded at a ceiling.

Figure 8D:
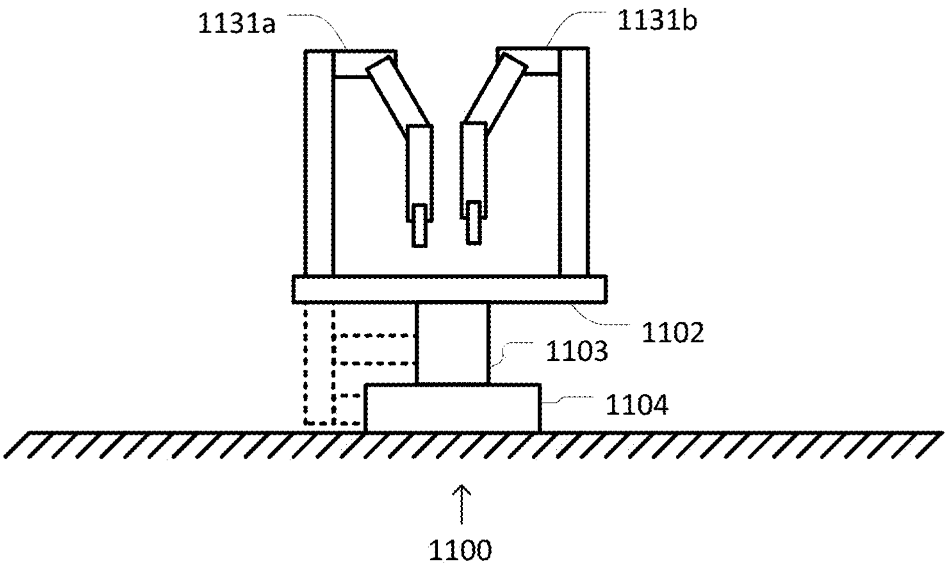

In addition, computer-assisted devices may be indirectly mechanically grounded via the movable surgical table 1100. As shown in FIG. 8D, a computer-assisted device 1131*a* is coupled to the table top 1102 of surgical table 1100. Computer-assisted device 1131*a* may optionally be coupled to other portions of surgical table 1100, such as table support structure 1103 or table base 1104, as indicated by the dashed structures shown in FIG. 8D. When table top 1102 moves with reference to table support structure 1103 or table base 1104, the computer-assisted device 1131*a* likewise moves with reference to table support structure 1103 or table base 1104. When computer-assisted device 1131*a* is coupled to table support structure 1103 or table base 1104, however, the base of computer-assisted device 1131*a* remains fixed with reference to ground as table top 1102 moves. As table motion occurs, the body opening where instruments are inserted into the patient may move as well because the patient's body may move and change the body opening locations relative to the table top 1102. Therefore, for embodiments in which computer-assisted device 1131*a* is coupled to the table top 1102, the table top 1102 functions as a local mechanical ground, and the body openings move with reference to the table top 1102, and so with reference to the computer-assisted device 1131*a* as well. FIG. 8D also shows that a second computer-assisted device 1131*b* optionally may be added, configured similarly to computer-assisted device 1131*a* to create a multi-instrument system. Systems that include one or more computer-assisted device coupled to the surgical table operate as disclosed herein.

In some embodiments, other combinations of computer-assisted devices with the same or hybrid mechanical groundings are possible. For example, a system may include one computer-assisted device mechanically grounded at the floor, and a second computer-assisted device mechanically grounded to the floor via the surgical table. Such hybrid mechanical ground systems operate as disclosed herein.

Figure 8E:
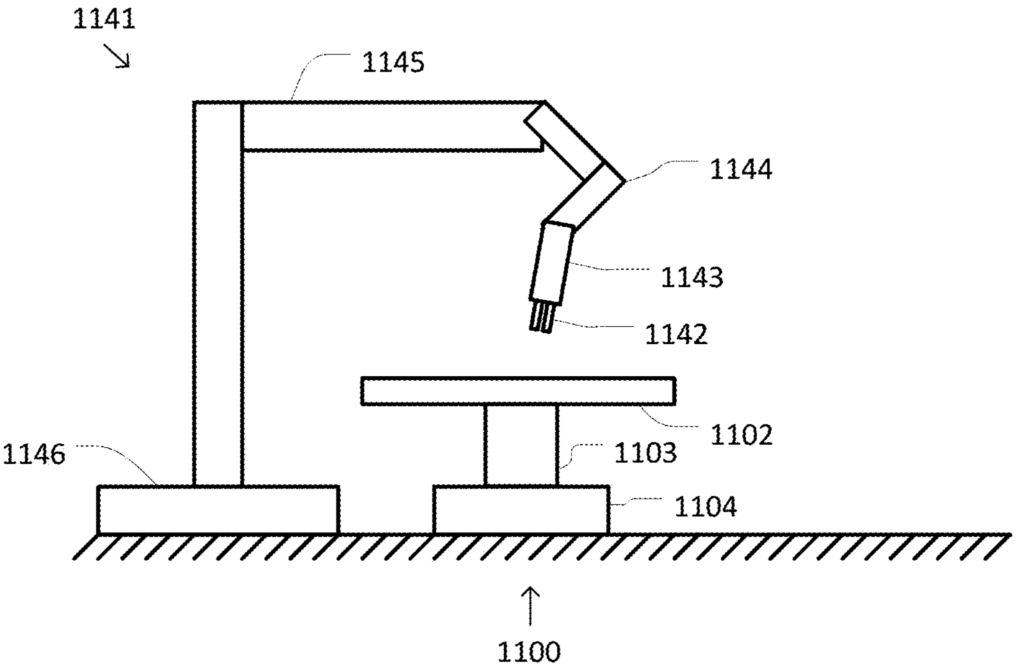

Inventive aspects also include single-body opening systems in which two or more surgical instruments enter the body via a single body opening. Examples of such systems are shown in U.S. Pat. No. 8,852,208 entitled "Surgical System Instrument Mounting," which was filed Aug. 12, 2010, and U.S. Pat. No. 9,060,678 entitled "Minimally Invasive Surgical System," which was filed Jun. 13, 2007, both of which are incorporated by reference. FIG. 8E illustrates a teleoperated multi-instrument computer-assisted device 1141 together with surgical table 1100 as described above. Two or more instruments 1142 are each coupled to a corresponding manipulator 1143, and the cluster of instruments 1142 and instrument manipulators 1143 are moved together by a system manipulator 1144. The system manipulator 1144 is supported by a support assembly 1145 that allows system manipulator 1144 to be moved to and fixed at various poses. Support assembly 1145 is mechanically grounded at a base 1146 consistent with the descriptions above. The two or more instruments 1142 are inserted into the patient at the single body opening. Optionally, the instruments 1142 extend together through a single guide tube, and the guide tube optionally extends through a cannula, as described in the references cited above. Computer-assisted device 1141 and surgical table 1100 operate together as described herein.

Figure 8F:
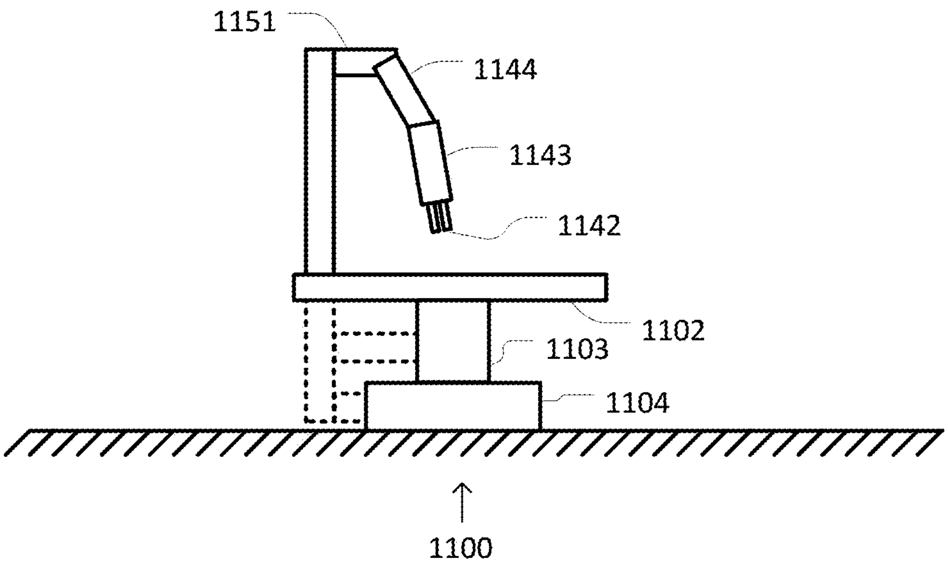

FIG. 8F illustrates another multi-instrument, single-body opening computer-assisted device 1151 mechanically grounded via the surgical table 1100, optionally by being coupled to table top 1102, table support structure 1103, or table base 1104. The descriptions above with reference to FIG. 8D also applies to the mechanical grounding options illustrated in FIG. 8F. Computer-assisted device 1151 and surgical table 1100 work together as described herein.

Figure 8G:
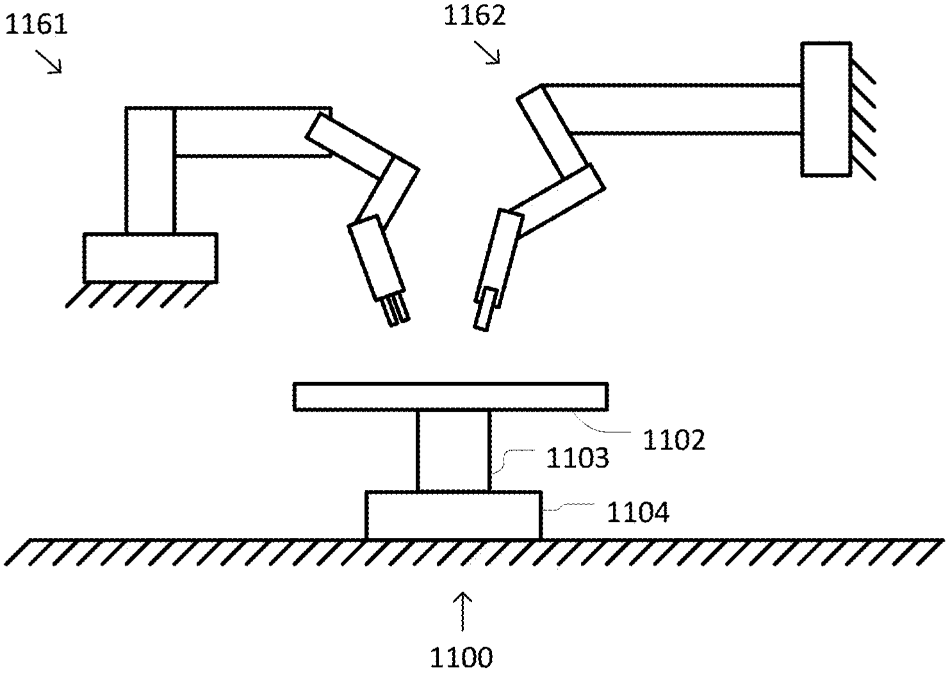

FIG. 8G illustrates that one or more teleoperated multi-instrument, single-body opening computer-assisted devices 1161 and one or more teleoperated single-instrument computer-assisted devices 1162 may be combined to operate with surgical table 1100 as described herein. Each of the computer-assisted devices 1161 and 1162 may be mechanically grounded, directly or via another structure, in various ways as described above.

Figure 3:
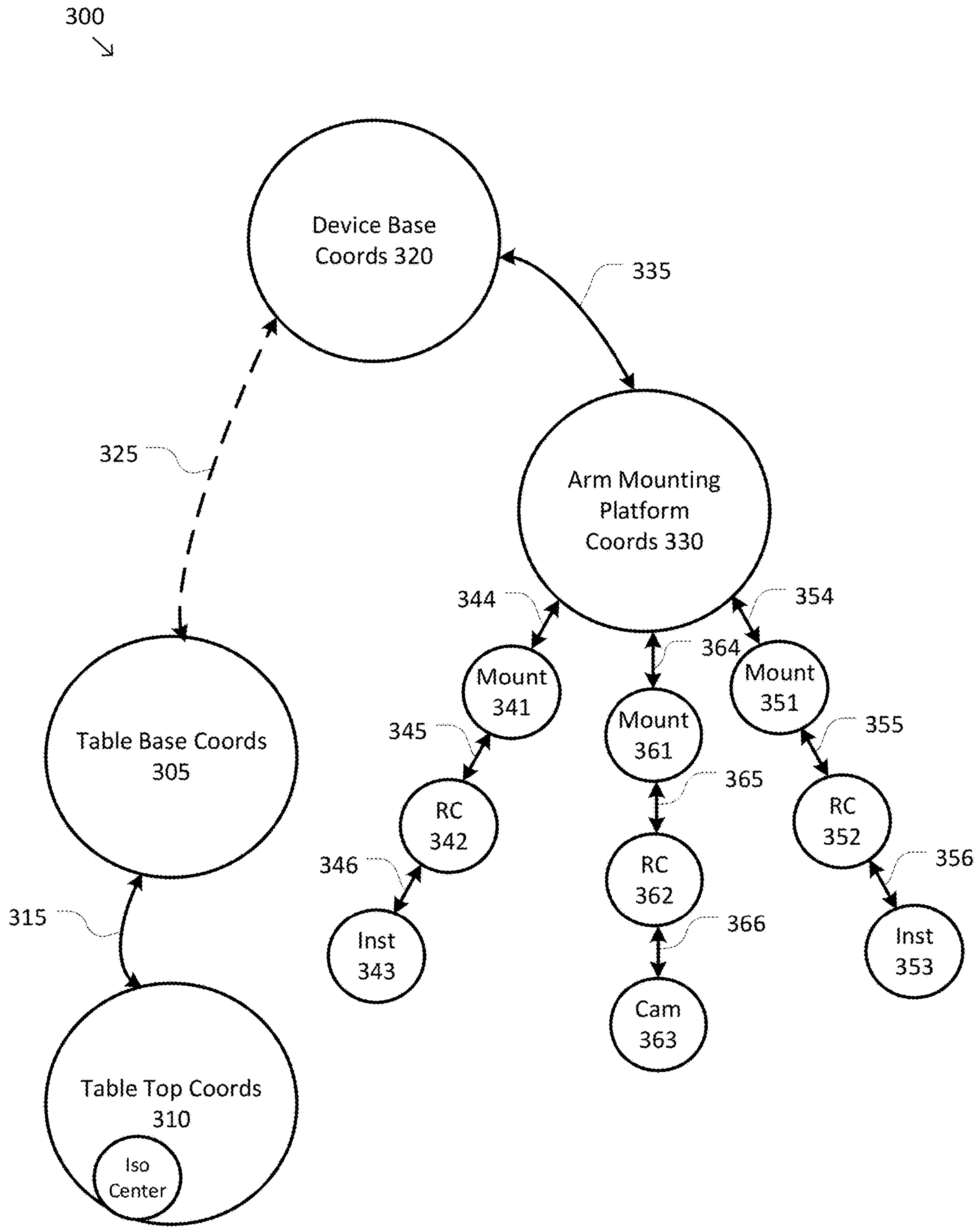
FIG. 3 is a simplified diagram of a kinematic model of a computer-assisted medical system according to some embodiments.

FIG. 3 is a simplified diagram of a kinematic model 300 of a computer-assisted medical system according to some embodiments. As shown in FIG. 3, kinematic model 300 may include kinematic information associated with many sources and/or devices. The kinematic information is based on known kinematic models for the links and joints of a computer-assisted medical device and a surgical table. The kinematic information is further based on information associated with the position and/or orientation of the joints of the computer-assisted medical device and the surgical table. In some examples, the information associated with the position and/or orientation of the joints may be derived from one or more sensors, such as encoders, measuring the linear positions of prismatic joints and the rotational positions of revolute joints.

The kinematic model 300 includes several coordinate frames or coordinate systems and transformations, such as homogeneous transforms, for transforming positions and/or orientation from one of the coordinate frames to another of the coordinate frames. In some examples, the kinematic model 300 may be used to permit the forward and/or reverse mapping of positions and/or orientations in one of the coordinate frames in any other of the coordinate frames by composing the forward and/or reverse/inverse transforms noted by the transform linkages included in FIG. 3. In some examples, when the transforms are modeled as homogenous transforms in matrix form, the composing may be accomplished using matrix multiplication. In some embodiments, a system may use the Denavit-Hartenberg parameters and conventions for attaching coordinate reference frames to one or more points in the kinematic chain and transforming from one reference frame to the other in the kinematic model 300. In some embodiments, the kinematic model 300 may be used to model the kinematic relationships of the computer-assisted device 210 and the surgical table 280 of FIG. 2.

The kinematic model 300 includes a table base coordinate frame 305 that is used to model a position and/or orientation of a surgical table, such as surgical table 170 and/or surgical table 280. In some examples, the table base coordinate frame 305 may be used to model other points on the surgical table relative to a reference point and/or orientation associated with the surgical table. In some examples, the reference point and/or orientation may be associated with a table base of the surgical table, such as the table base 282. In some examples, the table base coordinate frame 305 may be suitable for use as a world coordinate frame for the computer-assisted system.

The kinematic model 300 further includes a table top coordinate frame 310 that may be used to model positions and/or orientations in a coordinate frame representative of a table top of the surgical table, such as the table top 284. In some examples, the table top coordinate frame 310 may be centered about a rotational center or isocenter of the table top, such as isocenter 286. In some examples, the z-axis of the table top coordinate frame 310 may be oriented vertically with respect to a floor or surface on which the surgical table is placed and/or orthogonal to the surface of the table top. In some examples, the x- and y-axes of the table top coordinate frame 310 may be oriented to capture the longitudinal (head to toe) and lateral (side-to-side) major axes of the table top. In some examples, a table base to table top coordinate transform 315 is used to map positions and/or orientations between the table top coordinate frame 310 and the table base coordinate frame 305. In some examples, one or more kinematic models of an articulated structure of the surgical table, such as articulated structure 290, along with past and/or current joint sensor readings is used to determine the table base to table top coordinate transform 315. In some examples consistent with the embodiments of FIG. 2, the table base to table top coordinate transform 315 models the composite effect of the height, tilt, Trendelenburg, and/or slide settings associated with the surgical table.

The kinematic model 300 further includes a device base coordinate frame that is used to model a position and/or orientation of a computer-assisted device, such as computer-assisted device 110 and/or computer-assisted device 210. In some examples, the device base coordinate frame 320 may be used to model other points on the computer-assisted device relative to a reference point and/or orientation associated with the computer-assisted device. In some examples, the reference point and/or orientation may be associated with a device base of the computer-assisted device, such as the mobile cart 215. In some examples, the device base coordinate frame 320 may be suitable for use as the world coordinate frame for the computer-assisted system.

In order to track positional and/or orientational relationships between the surgical table and the computer-assisted device, it is often desirable to perform a registration between the surgical table and the computer-assisted device. As shown in FIG. 3, the registration may be used to determine a registration transform 325 between the table top coordinate frame 310 and the device base coordinate frame 320. In some embodiments, the registration transform 325 may be a partial or full transform between the table top coordinate frame 310 and the device base coordinate frame. The registration transform 325 is determined based on the architectural arrangements between the surgical table and the computer-assisted device.

In the examples of FIGS. 8D and 8F, where the computer-assisted device is mounted to the table top 1102, the registration transform 325 is determined from the table base to table top coordinate transform 315 and knowing where the computer-assisted device is mounted to the table top 112.

In the examples of FIGS. 8A-8C, 8E, and 8F, where the computer-assisted device is placed on the floor or mounted to the wall or ceiling, determination of the registration transform 325 is simplified by placing some restrictions on the device base coordinate frame 320 and the table base coordinate frame 305. In some examples, these restrictions include that both the device base coordinate frame 320 and the table base coordinate frame 305 agree on the same vertical up or z-axis. Under the assumption that the surgical table is located on a level floor, the relative orientations of the walls of the room (e.g., perpendicular to the floor) and the ceiling (e.g., parallel to the floor) are known it is possible for a common vertical up or z axis (or a suitable orientation transform) to be maintained for both the device base coordinate frame 320 and the table base coordinate frame 305 or a suitable orientation transform. In some examples, because of the common z-axis, the registration transform 325 may model just the rotational relationship of the device base to the table top about the z-axis of the table base coordinate frame 305 (e.g., a Oz registration). In some examples, the registration transform 325 may optionally also model a horizontal offset between the table base coordinate frame 305 and the device base coordinate frame 320 (e.g., a XY registration). This is possible because the vertical (2) relationship between the computer-assisted device and the surgical table are known. Thus, changes in a height of the table top in the table base to table top transform 315 are analogous to vertical adjustments in the device base coordinate frame 320 because the vertical axes in the table base coordinate frame 305 and the device base coordinate frame 320 are the same or nearly the same so that changes in height between the table base coordinate frame 305 and the device base coordinate frame 320 are within a reasonable tolerance of each other. In some examples, the tilt and Trendelenburg adjustments in the table base to table top transform 315 may be mapped to the device base coordinate frame 320 by knowing the height of the table top (or its isocenter) and the Oz and/or XY registration. In some examples, the registration transform 325 and the table base to table top transform 315 may be used to model the computer-assisted surgical device as if it were attached to the table top even when this is architecturally not the case.

The kinematic model 300 further includes an arm mounting platform coordinate frame 330 that may be used as a suitable model for a shared coordinate frame associated with the most proximal points on the articulated arms of the computer-assisted device. In some embodiments, the arm mounting platform coordinate frame 330 may be associated with and oriented relative to a convenient point on an arm mounting platform, such as the arm mounting platform 227. In some examples, the center point of the arm mounting platform coordinate frame 330 may be located on the arm mounting platform orientation axis 236 with the z-axis aligned with arm mounting platform orientation axis 236. In some examples, a device base to arm mounting platform coordinate transform 335 is used to map positions and/or orientations between the device base coordinate frame 320 and the arm mounting platform coordinate frame 330. In some examples, one or more kinematic models of the links and joints of the computer-assisted device between the device base and the arm mounting platform, such as the set-up structure 220, along with past and/or current joint sensor readings are used to determine the device base to arm mounting platform coordinate transform 335. In some examples consistent with the embodiments of FIG. 2, the device base to arm mounting platform coordinate transform 335 may model the composite effect of the two-part column, shoulder joint, two-part boom, and wrist joint of the set up structure of the computer-assisted device.

The kinematic model 300 further includes a series of coordinate frames and transforms associated with each of the articulated arms of the computer-assisted device. As shown in FIG. 3, the kinematic model 300 includes coordinate frames and transforms for three articulated arms, although one of ordinary skill would understand that different computer-assisted devices may include fewer and/or more articulated arms (e.g., one, two, four, five, or more). Consistent with the configuration of the links and joints of the computer-assisted device 210 of FIG. 2, each of the articulated arms are modeled using a manipulator mount coordinate frame, a remote center of motion coordinate frame, and an instrument, end effector, or camera coordinate frame, depending on a type of instrument mounted to the distal end of the articulated arm.

In the kinematic model 300, the kinematic relationships of a first one of the articulated arms is captured using a manipulator mount coordinate frame 341, a remote center of motion coordinate frame 342, an instrument coordinate frame 343, an arm mounting platform to manipulator mount transform 344, a manipulator mount to remote center of motion transform 345, and a remote center of motion to instrument transform 346. The manipulator mount coordinate frame 341 represents a suitable model for representing positions and/or orientations associated with a manipulator, such as manipulator 260. The manipulator mount coordinate frame 341 is typically associated with a manipulator mount, such as the manipulator mount 262 of the corresponding articulated arm. The arm mounting platform to manipulator mount transform 344 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 342 is associated with a remote center of motion of the instrument mounted on the manipulator, such as the corresponding remote center of motion 274 of the corresponding manipulator 260. The manipulator mount to remote center of motion transform 345 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the manipulator mount to remote center of motion transform 345 includes an essentially static translational component and a dynamic rotational component that changes as the manipulator and instrument are operated.

The instrument coordinate frame 343 is associated with an end effector located at the distal end of the instrument, such as the corresponding end effector 276 on corresponding instrument 270. The remote center of motion to instrument transform 346 is then based on one or more kinematic models of the links and joints of the computer-assisted device that move and/or orient the corresponding instrument and the corresponding remote center of motion, along with past and/or current joint sensor readings. In some examples, the remote center of motion to instrument transform 346 accounts for the orientation at which the shaft, such as the corresponding shaft 272, passes through the remote center of motion and the distance to which the shaft is advanced and/or withdrawn relative to the remote center of motion. In some examples, the remote center of motion to instrument transform 346 may further be constrained to reflect that the insertion axis of the shaft of the instrument passes through the remote center of motion and accounts for rotations of the shaft and the end effector about the axis defined by the shaft.

In the kinematic model 300, the kinematic relationships of a second one of the articulated arms is captured using a manipulator mount coordinate frame 351, a remote center of motion coordinate frame 352, an instrument coordinate frame 353, an arm mounting platform to manipulator mount transform 354, a mount to remote center of motion transform 355, and a remote center of motion to instrument transform 356. The manipulator mount coordinate frame 351 represents a suitable model for representing positions and/or orientations associated with a manipulator, such as manipulator 260. The manipulator mount coordinate frame 351 is associated with a manipulator mount, such as the manipulator mount 262 of the corresponding articulated arm. The arm mounting platform to manipulator mount transform 354 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 352 is associated with a remote center of motion of the manipulator of an articulated arm, such as the corresponding remote center of motion 274 of the corresponding manipulator 260. The mount to remote center of motion transform 355 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the mount to remote center of motion transform 355 includes an essentially static translational component that does not change as the manipulator and instrument are operated and a dynamic rotational component that changes as the manipulator and instrument are operated.

The instrument coordinate frame 353 is associated with a point on an end effector, instrument, instrument, and/or end effector on an instrument mounted on the articulated arm, such as the corresponding end effector 276 on corresponding instrument 270. The remote center of motion to instrument transform 356 is then based on one or more kinematic models of the links and joints of the computer-assisted device that move and/or orient the corresponding instrument and the corresponding remote center of motion, along with past and/or current joint sensor readings. In some examples, the remote center of motion to instrument transform 356 accounts for the orientation at which the shaft, such as the corresponding shaft 272, passes through the remote center of motion and the distance to which the shaft is advanced and/or withdrawn relative to the remote center of motion. In some examples, the remote center of motion to instrument transform 356 may be constrained to reflect that the insertion axis of the shaft of the instrument passes through the remote center of motion and may account for rotations of the shaft and the end effector about the insertion axis defined by the shaft.

In the kinematic model 300, the kinematic relationships of a third one of the articulated arms is captured using a manipulator mount coordinate frame 361, a remote center of motion coordinate frame 362, a camera coordinate frame 363, an arm mounting platform to manipulator mount transform 364, a mount to remote center of motion transform 365, and a remote center of motion to camera transform 366. The manipulator mount coordinate frame 361 represents a suitable model for representing positions and/or orientations associated with a manipulator, such as manipulator 260. The manipulator mount coordinate frame 361 is associated with a manipulator mount, such as the manipulator mount 262 of the corresponding articulated arm. The arm mounting platform to manipulator mount transform 364 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 362 is associated with a remote center of motion of the manipulator of the articulated arm, such as the corresponding remote center of motion 274 of the corresponding manipulator 260. The mount to remote center of motion transform 365 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the mount to remote center of motion transform 365 includes an essentially static translational component that does not change as the manipulator and instrument are operated and a dynamic rotational component that changes as the manipulator and instrument are operated.

The camera coordinate frame 363 is associated with an imaging device, such an endoscope, mounted on the articulated arm. The remote center of motion to camera transform 366 is then based on one or more kinematic models of the links and joints of the computer-assisted device that move and/or orient the imaging device and the corresponding remote center of motion, along with past and/or current joint sensor readings. In some examples, the remote center of motion to camera transform 366 accounts for the orientation at which the shaft, such as the corresponding shaft 272, passes through the remote center of motion and the distance to which the shaft is advanced and/or withdrawn relative to the remote center of motion. In some examples, the remote center of motion to camera transform 366 may be constrained to reflect that the insertion axis of the shaft of the imaging device passes through the remote center of motion and accounts for rotations of the imaging device about the axis defined by the shaft.

In some embodiments, an imaging device associated with camera coordinate frame 363 may stream video to an operator workstation such that a user may view the video stream from camera coordinate frame 363. For example, the video captured by the imaging device may be relayed and displayed on display system 192 of operator workstation 190 of FIG. 1. In some embodiments, the imaging device may be oriented such that it captures video and/or images of an instrument associated with instrument coordinate frame 343 and/or an instrument associated with instrument coordinate frame 353. The instrument associated with instrument coordinate frame 343 and/or the instrument associated with instrument coordinate frame 353 may be operated by the user through a controller, such as input or master controls 195 of FIG. 1. In some embodiments, to allow for intuitive manipulation of the instruments and/or end effectors, user commands from the controls may correlate with the coordinate system of the camera coordinate frame 363. For example, commands of up and down, left and right, and in and out using the controllers may translate to movements of the instrument up and down, left and right, and in and out in relation to camera coordinate frame 363. Up and down, left and right, in and out, may be resented by the x, y, and z translational axis of coordinate frame 363. Similarly, roll, pitch, and yaw commands may cause the instrument to roll, pitch, and yaw in relation to the camera coordinate frame. In some embodiments, one or more processors, such as processor 140 of FIG. 1, may translate user commands from the camera coordinate frame 363 to respective commands and motion in the instrument coordinate frames 343 and 353. The translational commands may be through the kinematic relationships. For example, commands to the instrument associated with instrument coordinate frame 343 may go from camera coordinate frame 363 to remote center of motion reference frame 362 using transform 366, then from remote center of motion reference frame 362 to mount coordinate frame 361 using transform 365, mount coordinate frame 361 to arm mounting platform coordinate frame 330 using transform 364, arm mounting platform coordinate frame 330 to manipulator mount coordinate frame 341 using transform 344, manipulator mount coordinate frame 341 to remote center of motion coordinate frame 342 using transform 345, and remote center of motion coordinate frame 342 to instrument coordinate frame 343 using transform 346. In this manner, any motion commands known in one reference frame can be transformed to corresponding commands in one or more other coordinate frames.

As discussed above and further emphasized here, FIG. 3 is merely an example which should not unduly limit the scope of the claims. One of ordinary skill in the art would recognize many variations, alternatives, and modifications. According to some embodiments, the registration between the surgical table and the computer-assisted device may be determined between the table top coordinate frame 310 and the device base coordinate frame 320 using an alternative registration transform. When the alternative registration transform is used, registration transform 325 is determined by composing the alternative registration transform with the inverse/reverse of the table base to table top transform 315. According to some embodiments, the coordinate frames and/or transforms used to model the computer-assisted device may be arranged differently dependent on the particular configuration of the links and joints of the computer-assisted device, its articulated arms, its end effectors, its manipulators, and/or its instruments. According to some embodiments, the coordinate frames and transforms of the kinematic model 300 may be used to model coordinate frames and transforms associated with one or more virtual instruments and/or virtual cameras. In some examples, the virtual instruments and/or cameras may be associated with previously stored and/or latched instrument positions, projections of instruments and/or cameras due to a motion, reference points defined by a surgeon and/or other personnel, and/or the like.

As a computer-assisted system, such as computer-assisted systems 100 and/or 200 are being operated, one of the goals is to minimize and/or eliminate the propagation of disturbances and/or movements from one or more joints and/or links to the position of one or more points of an instrument (s), link(s), and or joint(s). For example, referring to FIG. 2, a disturbance to one or more of joints 242 and/or links 246 may cause an injury to patient 278 if the disturbance propagated to end effector 276 (end effector 276 being an exemplary point of interest) while inside of patient 278.

In one mode of operation for the computer-assisted system, one or more joints of the surgical table and joints of the articulated arms may be locked and/or held in place through the use of servo control and/or brakes so that motion of the joints is limited and/or prohibited entirely. In some examples, this may allow the joints of the manipulators to control an instrument undisturbed by motion from other joints when accomplishing a desired procedure. In some embodiments, the manipulators may be physically constrained to maintain a remote center of motion and motion of one or more joints that do not make up the manipulator might undesirably cause the remote center of motion to move. In those examples, it may be beneficial to have the joints that do not make up the manipulators be locked in place through physical and/or servo control braking systems. However, there may be instances where allowing movement to the remote center of motion would be desirable, and thus allowing for release of the brakes locking one or more of the joints that may affect the position of the remote center of motion.

In some examples, the instruments may be inserted through a body opening of a patient during a procedure. In some examples, the position of the instruments may be controlled via teleoperation by a surgeon at an operator console such as workstation 190 of FIG. 1. It may, however, be desirable to support other modes of operation for the computer-assisted system that allow for movement in the articulated arms while the instruments remain inserted through a body opening of the patient. These other modes of operation may introduce risks that are not present in modes of operation when the instruments are not inserted into a body opening of the patient. In some examples, these risks may include but at not limited to injury to the patient when the instruments are allowed to move relative to the patient, the instruments breaching a sterile field, damage from collisions between the articulated arms, and/or the like.

In a general case, these other modes of operation may be characterized by a goal of maintaining a point of an instrument inserted into an opening of a patient relative to a patient when one or more joints proximal to the instrument are subject to a disturbance that results in a change to positions and/or orientations (i.e., movements) of the one or more joints. Because disturbances in one or more first or disturbed joints proximal to an instrument results in a change in the position of the instrument, it may be desirable to introduce movement in one or more second or compensating joints that compensate for the movement of the instrument caused by the movement of the disturbed joints. Determining the extent of the disturbance and the amount of compensation depends on the type and nature of the disturbance, such as whether the disturbance is associated with movement of the surgical table or patient, or whether the disturbance is confined to the articulated arm used to control the instrument.

In one category of these other modes of operation is when the patient is not moving so that the position of the instrument and/or a point on the instrument may be monitored and maintained in any suitable world coordinate frame. This may include disturbances associated with controlled motion of the articulated arm. In some examples, the controlled motion of the articulated arm may include movement in one or more joints used to set-up the articulated arm and/or the manipulator before performing a procedure. One example of this includes the movement of one or more of the set-up structures of a computer-assisted device consistent with the embodiments of FIG. 2 where the arm mounting platform 227 is translated and aligned to allow the set-up joints 240 be moved to provide good range of motion in the manipulator 260 during a procedure. Examples of this type of motion is described in greater detail in U.S. Provisional Patent Application No. 61/954,261 entitled "System and Method for Aligning with a Reference Target," which was filed on Mar. 17, 2014 and which is hereby incorporated by reference. This category may further include disturbances associated with the release of brakes and/or other joint locks prior to initiating other motion. In some examples, external forces and/or torques on the shaft of the instrument, such as due to forces and torques applied to the instrument by the body wall of the patient while inserted into the patient, may result in undesirable motion of the instrument when the brakes and/or locks are released and forces and/or torques are absorbed by the released joints. This category may further include disturbances caused by operation of the articulated arm in a clutched or float state such as might occur during manual repositioning of the articulated arm by an operator and/or due to a collision between the articulated arm and an obstacle. Examples of this type of motion are described in greater detail in U.S. Provisional Patent Application No. 91/954,120 entitled “System and Method for Breakaway Clutching in an Articulated Arm,” which was filed on Mar. 17, 2014 and which is hereby incorporated by reference. Additional examples of this type of motion may occur when the computer-assisted device prepares for integrated surgical table motion by releasing one or more brakes or locks and the forces and torques applied to the instruments inserted into a body opening by the body wall are released. These types of motions and disturbances are described in greater detail in U.S. Provisional Patent Application No. 62/134,207 entitled “System and Method for Integrated Surgical Table,” which was filed Mar. 17, 2015 and concurrently filed PCT Patent Application No. PCT/US2015/057656 entitled “System and Method for Integrated Surgical Table” and published as WO2016/069648 A1, both of which are hereby incorporated by reference in their entirety.

With respect to brake releases on one or more joints of an articulated arm, any forces and/or torques being applied to the joint upon the brake release may cause motion to the joints and their respective links. These disturbances may often cause quick and sometimes large jumps in movements to the end effectors and/or instruments attached to the articulated arms. Though any single disturbance from a single brake release may be small, the combined disturbances when brakes for multiple joints are released simultaneously may be rather large. These large jumps in movement may cause the end effectors to injure the patient. Furthermore, these jumps in movement are often too quick for human reactions, and therefore, difficult, if not impossible, to remedy through manual control. One method to reduce the jumps and provide users the ability to react would be to slowly reduce the braking force for each brake over time and/or release the brakes one at a time. However, during surgical operations, it is important to minimize any unnecessary time consumption because mortality rates of a patient during surgery go up in relation to the length of time the patient is in surgery. Therefore, it is desirable to release brakes within a short period of time (over a few seconds or less).

Figure 4:
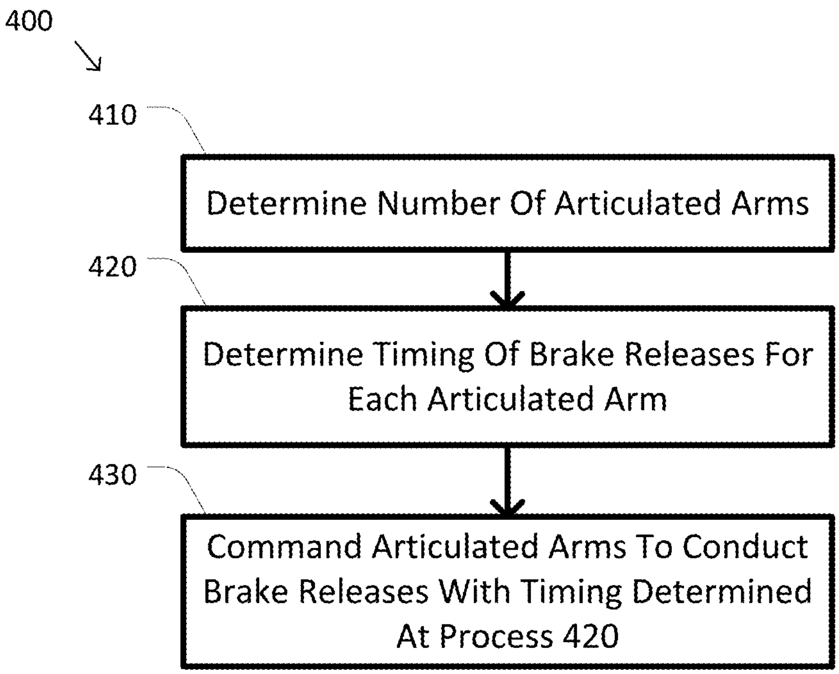
FIG. 4 is a simplified diagram of a method of staggering the release of brakes on an articulated arm.

FIG. 4 is a simplified diagram of an exemplary method 400 for a staggered brake release according to some embodiments. In some examples, method 400 may be used to stagger the release of one or more brakes on joints of one or more articulated arms, such as articulated arms 120 of FIG. 1. According to some embodiments, method 400 may include one or more of the processes 410-430 which may be implemented, at least in part, in the form of executable code stored on a non-transitory, tangible, machine readable media that when run on one or more processors (e.g., the processor 140 in control unit 130 of FIG. 1) may cause the one or more processors to perform one or more of the processes 410-430.

At process 410, the number of articulated arms for brake release is determined. In some embodiments, the number of articulated arms may be predetermined. For example, the device may be hard coded with a specific number of articulated arms. In some embodiments, a user may set the number of articulated arms set for brake releases. For example, using buttons and/or switches on a workstation, such as workstation 190 of FIG. 1, a user and/or operator may be able to select which arms and/or the number of arms that will have brakes released. In some embodiments, the number of articulated arms may be detected by connections to one or more ports and/or other communications interfaces. For example, a computer aided system, such as computer aided system 100 of FIG. 1, may have a brake release mode for releasing one or more brakes in the articulated arms and control unit 130 may determine the number of articulated arms controlled by the system through the communication interfaces with the articulated arms.

A process 420, the timing of brake releases for each articulated arm is determined. In some embodiments, the timing of each brake release may be staggered to ensure no single brake is released at the same time as another brake. In some embodiments, the joints on an articulated arm may be set to automatically release brakes in quick succession and a central controller, such as control unit 130 of FIG. 1, may determine how to stagger the start of each brake release for each arm. For example, an articulated arm, such as articulated arm 120 of FIG. 2 may have brakes being released for a set of joints, such as setup joints 240 of FIG. 2. Assuming there are four setup joints, these joints may be released in quick succession, such as released every 0.25 seconds. The time between release of different brakes and the order in which brakes are released may be preset and automatic once instructions for brake release are received. This allows for quick reliable brake releases without the delays of communication and processing times.

To ensure that no brake release for any single articulated arm is released at the same time as a brake release for another articulated arm, the command to begin brake release for each arm is sent at a calculated interval that prevents simultaneous brake release. For example, each arm may be ordered to begin brake release 0.25 seconds from each other when the interval between brake releases in each articulated arm is 0.2 seconds. In this example, the four joints released in the first arm will be released at time 0 s, 0.2 s, 0.4 s, and 0.6 s. The release of the brakes for the next arm and the four joints of the next arm would be 0.25 s, 0.45 s, 0.65 s, and 0.85 s. The third arm would release brakes at 0.5 s, 0.7 s, 0.9 s, and 1.1 s. Finally, the fourth arm would release at 0.75 s, 0.95 s, 1.15 s, and 1.35 s. One of ordinary skill in the art would recognize that there are many possibilities for brake release intervals and intervals between commands such that no brake is released at the same time, all of which are contemplated herein. One simple exemplary method of determining when each arm begins brake release would be to divide the time interval between brake releases on an arm by the number of arms.

In some embodiments, the order of brake release is predetermined. For example, the brakes may be released in the order of brakes for joints that have the least motion to the brakes for joints that have the most motion. In some embodiments, determining which joints cause or move the most during a brake release may be determined through empirical tuning. Based on experimentation, releasing brakes for rotational joints and/or translational joints for motion parallel to the floor (sometimes referred to as joints with horizontal motion) tend to cause the least amount of motion and releasing brakes for joints that allow movement perpendicular to the floor (sometimes referred to as joints with vertical motion) tend to cause the most motion. In some embodiments, a force sensor may indicate which brakes are bearing the most force and/or torque and determine that those joints will move the most. In some embodiments, the order of brake release may be determined based on the configuration and position of each joint. For example, joints at the end of its range of motion may be less likely to move when a brake for the joint is released.

In some embodiments, an articulated arm may not be in communications with any other articulated arm. Thus, when there are brakes release commands sent to one or more arms is delayed, this may cause one or more joints to be released simultaneously. In some examples, to ensure simultaneous brakes releases don't occur, each robotic arm may share a global clock cycle count for the entire system and each arm may be given a window of time for which brakes can be released. For example, if a system were to have the brake release of all arms to begin within a one second time frame, a 1 kHz processor would have 1000 clock cycles within that time frame. If there were four articulated arms, the clock cycles within one second can be divided into four windows of 250 cycles. Cycles 0-249 can be designated for one arm, 250-499 for the second arm, 500-749 for the third arm, and 750-999 for the fourth arm. The timing window can then be determined by the modulo of the global clock cycle by 1000. In this manner, each window is repeated once every 1000 clock cycles. When an arm misses a window for brake release in a clock cycle, the brake release for that articulated arm will release when the 250 clock cycle window for that articulated arm repeats.

More generally, windows of time for brake release is determined by dividing the number of clock cycles for a time limit by the number of arms. The brake release window for a given global clock time is determined by using the modulo of the global clock by the number of clock cycles for the time limit. In some embodiments, buffers may be added to each clock cycle window to prevent brake releases occurring within one clock cycle of each other. For example, based on the 250 clock cycle window, the window for brake release may be a single clock cycle for each arm at 249, 499, 749 and 999. In this manner there is a 249 clock cycle buffer between when brake release begins for each articulated arm, or approximately 0.25 seconds based on the 1 kHz processor.

In some embodiments, the central controller directly determines which brake is released, the order of the brake releases, and when. In this manner, the central control can ensure that none of the brakes are released at the same time. In some embodiments the brakes may be gradually released over time. However, method 400 is set up to also work with binary brakes without a gradual reduction in braking force. This allows the method to be used with cheaper less complex brakes that are present in legacy systems. Furthermore, binary brakes are desirable for being cheaper, more reliable, and simpler.

At process 430, the brakes to joints of the articulated arms are released in accordance with the brake release timing set up at process 420.

In some embodiments, the joints of the articulated arms may have brakes that may be gradually released. In some examples each of the brakes could be concurrently released gradually over time. In some embodiments, brakes may be released in accordance with the timing determined at process 420 with the brakes gradually releasing within an allotted timing window and/or with gradual brake release beginning at the beginning of the allotted timing window. In some examples, the gradual release of the brakes may be accomplished by ramping a signal that controls braking force over time. In some examples, the ramped signal may be a voltage, a current, a pulse-width duty cycle, and/or the like. Depending of a transfer relationship between the ramped signal and the braking force, the change in value of the ramped signal over time may be linear and/or non-linear.

Figure 5:
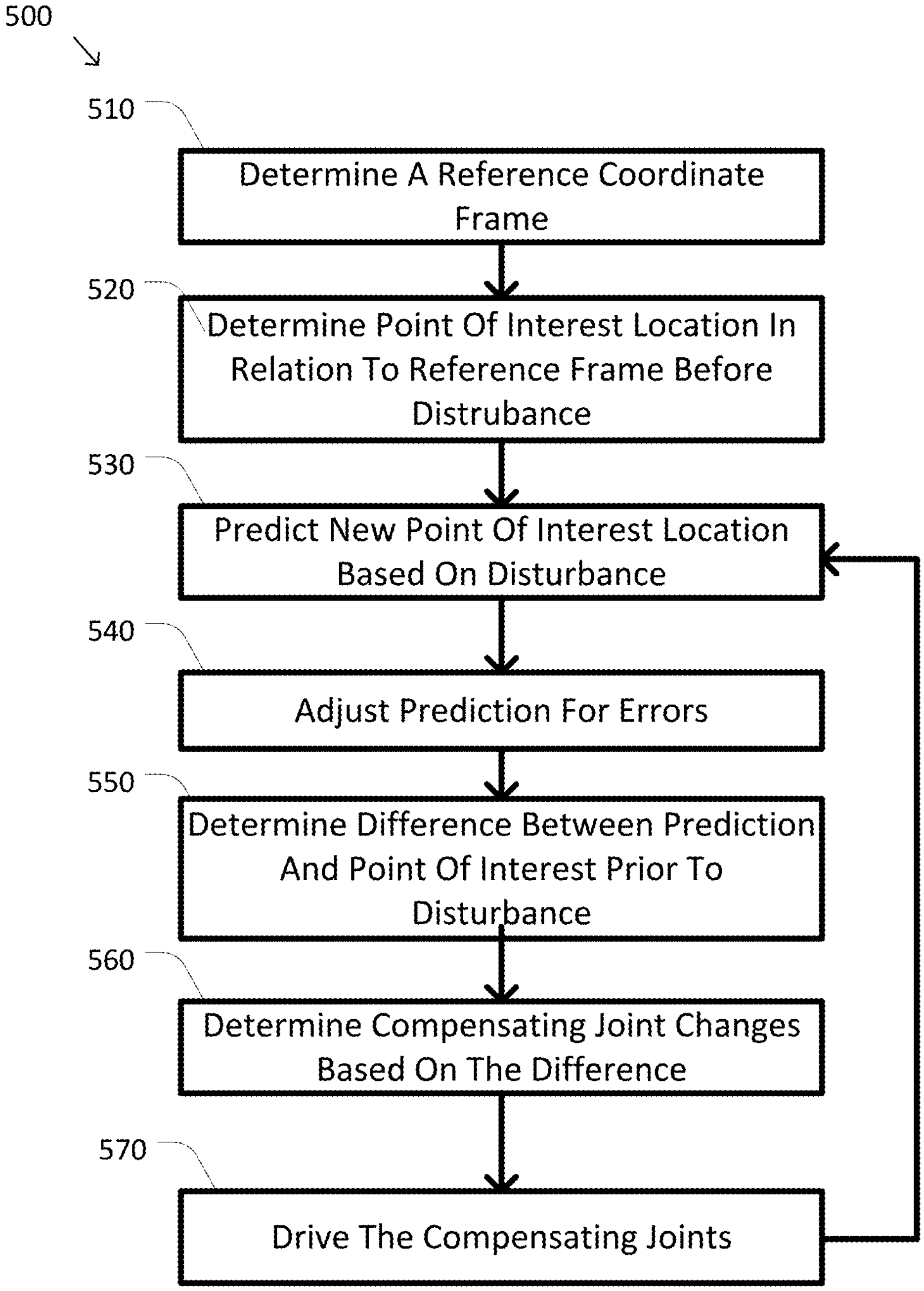
FIG. 5 is a simplified diagram of a method of compensating disturbances from one joint set to a point of interest with a second joint set.

FIG. 5 is a simplified diagram of a method 500 for compensating for disturbances, such as disturbances caused by a brake release according to some embodiments. In some examples, the disturbances caused by the release of brakes for one or more joints, collectively referred to as a first set of joints or disturbed joints, may be compensated for by one or more other joints, collectively referred to as a second set of joints or compensating joints, such that a point associated with an articulated arm (point of interest) and/or instrument is minimally or completely unaffected by the disturbance. The point of interest may be the location of a particular joint, remote center of motion, instrument, end effector, instrument, an end effector, a point along a kinematic chain, an approximation of any of the preceding points, and/or the like. In some embodiments, the compensating joints may provide one or more redundant degrees of freedom that are used to compensate for movement caused by the changes in the disturbed joints.

In some examples the disturbed joints may all be distal or proximal to the point of interest in comparison to the compensating joints. For example, the series of set-up joints 240 of FIG. 2 may be the disturbed joints, joints 264 may be the compensating joints, and end effector 276 may be the point of interest. In this example, set-up joints 240 are more distal from end effector 276 than joints 264 of manipulator 260, which may be the compensating joints.

In other examples some of the disturbed joints may be between compensating joints. In these examples, however, the kinematic chain may be broken into subsets of joints and connectors such that each subset has all the disturbed joints in the subset as proximal or distal to a subset point of interest (which may or may not be the same point of interest for the entire kinematic chain) in comparison to the compensating joints within the subset. In this manner, the model for compensating disturbed joints all being more distal or proximal to a point of interest in relation to all compensating joints can be applied to kinematic chains where some of the disturbed joints are more proximal and some of the disturbed joints are more distal to a point of interest in relation to one or more compensating joints by breaking the kinematic chain into sub-kinematic chains.

Method 500 is discussed in the context of embodiments where all of the disturbed joints are more proximal to the point of interest than the compensating joints in the kinematic chain. However, one of ordinary skill in the art would understand that this method is applicable to situations where all of the disturbed joints are more distal rather than proximal to the compensating joints. Furthermore, as discussed above, this method can also be applied in situations where the disturbed joints are interleaved among the compensating joints in a kinematic chain by treating the entire kinematic chain as a collection of sub-kinematic chains wherein each sub-kinematic chain may be chosen such that all of the disturbed joints are proximal or distal to the compensating joints in relation to one or more points of interest.

Method 500 may include one or more of the processes 510-560 which may be implemented, at least in part, in the form of executable code stored on a non-transitory, tangible, machine readable media that when run on one or more processors (e.g., the processor 140 in control unit 130 of FIG. 1) may cause the one or more processors to perform one or more of the processes 510-560.

In some embodiments, method 500 may be used to compensate for changes in the position of the instrument due to motion in one or more disturbed joints by introducing compensating motion in one or more compensating joints. In some examples, method 500 may be used when the motion in the disturbed joints is due to controlled motion, clutched motion, brake or lock release, and/or the like. In some examples, method 500 may be used when motion in the disturbed joints is due to the release of a brake, such as during process 430. In some examples consistent with the embodiments of FIG. 2, the one or more disturbed joints and/or the one or more compensating joints may include any of the joints in set-up structure 220, the set-up joints 240, and/or any joints of manipulator 260 proximal to the instrument. In some embodiments, use of method 500 may be limited to operation when an instrument, cannula, and/or the like is coupled to the distal end of a corresponding articulated arm, end effector, and/or manipulator so that a remote center of motion for the articulated arm, end effector, and/or manipulator may be defined. In some embodiments, method 500 may include having the pose and/or position of the instrument at least partially maintained using resistance from the wall of an orifice or incision of a patient and/or by an operator of the computer-assisted device. In some embodiments, method 500 may be applied in conjunction with and/or on top of movement commands from an operator of the computer-assisted device such that the operator still has control over the movement of one or more instruments.

At a process 510, a reference coordinate frame is established. For case of calculations, process 510 may use a non-moving/fixed point in a kinematic chain as a reference frame. For example, with respect to FIGS. 2 and 3, if setup joints 240 are the disturbed joints, and the joints of manipulator 260 are the compensating joints, any point more proximal to cart 215 than the setup joints 240 could be used as a reference frame, including joint 226 which may be the arm mounting platform coordinate frame 330 of FIG. 3.

At a process 520, a reference transform from the reference coordinate frame to a point for steadying, such as end effector 276 of FIG. 2, is established. This reference transform may be established prior to any disturbances to the disturbed joints. In some embodiments, this transform may be a transform for a particular position of one or more joints, instruments, links, and/or any other object in a kinematic chain. In some embodiments, the reference transform may be made up of several sub-transforms between several coordinate frames. For example, the transform from arm mounting platform coordinate frame 330 to instrument coordinate frame 353 is made up of transforms 354, 355, and 356. In some embodiments, these transforms may be stored in memory, such as memory 150 of FIG. 1.

At process 530, the disturbances in the joints are detected and a prediction of the movement to the point of interest caused by the disturbance is determined using the new position of the disturbed joints.

The following is an exemplary method of determining a disturbance to a point of interest caused by the disturbance in the disturbed joints. At a first step, a transform between two coordinate frames spanning the disturbed joints before disruption may be stored in memory, such as memory 150 of FIG. 1. In some examples, the two coordinate frames span the disturbed joints when a first one of the coordinate frames is proximal to the most proximal of the disturbed joints and the second one of the coordinate frames is distal to the most distal of the disturbed joints. In a second step, a transform between two coordinate frames spanning the compensating joints may be stored in memory. In a third step, a location for an undisturbed point of interest is determined using the saved transforms in the first and second steps. In some examples, this location of the point of interest may model the point of interest before any disturbed or compensating motion takes place. In a fourth step, an estimated location for the point of interest is determined by using a live/current transform between the two coordinate frames spanning the disturbed joints and the saved transform in the second step. In some examples, an estimated location of the point of interest that accounts for the changes in the disturbed joints, but not the compensating joints may be determined. In a fifth step, the difference between the location for the undisturbed point of interest and the estimated point of interest can be used to determine how the motion of the disturbed joints has moved the point of interest. As would be recognized by one of ordinary skill in the art, the stored transform between the two coordinate frames spanning the compensating joints may be stored in any suitable data structure capable of representing a homogenous transform, such as in the form of a matrix, and/or the like. In some examples, the transform may be stored as joint angles and/or positions from which the transform may be recomputed using one or more kinematic models of the compensating joints. The stored transform may be conducted for a particular configuration and/or a configuration for a particular point in time. An exemplary application of this method to FIG. 3 may include the following, joint motions caused by a disturbance may change transform 354 but not transforms 355 and 356. In this manner, a prediction of the change in position caused by the disturbance can be determined by using the changed transform 354 and the saved transforms 355 and 356. Furthermore, this allows isolation of the motion of the instrument reference frame 353 caused by the disturbance from actuated motion caused by user commands. Therefore, even though saved transforms 355 and 356 may not be used for determining the actual position of an instrument, it can be used to predict a motion to a point of interest caused by a disturbance.

At an optional process 540, the prediction of at 530 is adjusted for real world errors. In a perfect world, where all links between joints are perfectly ridged, the prediction at process 530 would be a perfect match to where the point of interest moved due to the disturbances in the joints. However, the links between joints bend and give depending on the amount of force applied to the links and the flexural strength of the link material. For example, during a surgical operation the skin of the operating subject will often tent or ride up the cannula entering the subject. This tenting will apply a force onto the cannula, which in turn applies a force onto the links and joints of the device. While the brakes are engaged, the skin is held up by the device to maintain its position, but when the brakes are released for some of the joints, those joints will be allowed to move freely and be disturbed. In turn, the tented skin will move the released joints until the skin is no longer applying a force in the direction of movement of the joint. Because the skin is no longer applying a force (or applying less force) on the cannula the links between joints that were bearing forces caused by the tenting will de-flex. The de-flexing will often counteract some of the motion by the joints, thus causing movement predictions based on joint movements to be an over estimate. This may cause an error in the prediction at process 530. At process 540, adjustments are made to account for this source of error and other sources of errors to the prediction.

In some embodiments, error correction may be a scalar multiple estimating the amount of error in the translational motion predicted during process 530. The estimates may depend on one or more factors such as the patient, procedure, and/or orientation of the articulated device. For example, there may be settings for child, adult, veterinary (e.g. animal species), area of surgery (e.g. arm, leg, stomach, chest, cranial, etc.), and or the like. In some examples, a general error estimate may be used for all cases. In some embodiments, a single error estimate between 80-95% (e.g., 85%) of the translational motion and 100% of the rotational motion predicted during process 530 for the disturbance at the point of interest may be used as the error corrected position of the point of interest. For case of calculations, the error correction may be computed at the coordinate frame of the point of interest. In this manner, corrections to translational motion on the point of interest may be treated differently than rotational errors (e.g., using one fraction of the predicted translational disturbance and another fraction for the predicted rotational disturbance). Though the corrections may be applied at a different reference frames, the computations may become difficult because the rotation in another coordinate frame contributes to translational motion in the coordinate frame of the point of interest. In some embodiments, when process 540 is omitted, the prediction determined during process 530 may be used as the error corrected prediction. Using the prediction determined during process 530 may, however, introduce a slight over correction.

At a process 550, differences between the error corrected predicted transform and the reference transform are determined. The differences between the error corrected predicted transform determined during process 540 and the reference transform determined during process 520 represent errors that are being introduced into the point of interest by the disturbance. Unless the errors are compensated for by movement using one or more compensating joints of the articulated arm, the placement of the point of interest may undesirably change. In some examples, the differences may be determined by multiplying corresponding matrices and/or vector representations of the actual and reference transforms. In some examples, the differences may be represented as an error transform determined by composing an inverse/reverse of the reference transform with the error corrected prediction transform.

At a process 560, compensating joint changes are determined based on the differences. Using the differences between the actual transform and the reference transform determined during process 550, changes in the one or more compensating joints are determined. The differences between the error corrected predicted transform and the reference transform is mapped from the reference coordinate system of the reference transforms to one or more local coordinate systems associated with each of the compensating joints. In effect, this transforms the errors in the placements of the point of interest from the reference coordinate system to relative errors of the point of interest relative to the compensating joints. In some examples, one or more kinematic models are used to transform the differences to the local coordinate systems. In some examples, the compensating joints may include any of the joints of the articulated arm and/or the manipulator that are not one of the disturbed joints. Once the relative errors of the point of interest are determined, they may be used to determine the movements for each of the compensating joints. In some examples, an inverse Jacobian may be used to map the relative errors to the movements of the compensating joints. In some examples, the movements in the compensating joints may be applied as joint velocities applied to the compensating joints.

At a process 570, the compensating joints are driven. One or more commands are sent to the one or more actuators in the compensating joints based on the movements of the compensating joints determined during process 560. The commands sent to the compensating joints correct for the disturbances to the point of interest introduced by the movements in the one or more disturbed joints so that placement of the point of interest in the reference coordinate system is maintained with little or no disturbance. As long as the one or more compensating joints continue to make corrective changes to the placement of the point of interest, processes 530-570 may be repeated to compensate for any errors introduced into the position and placement of the point of interest.

According to some embodiments, correcting, driving, or moving the point of interest may be conducted from a reference point different from the point of interest. This may allow for simpler computations and/or reuse of functions and/or algorithms for driving joint movements, such as joint positioning and velocity. For example, referring to FIG. 2, it may be computationally easier to have joints of the manipulator 260 of computer-assisted system 200 adjust for errors at manipulator mount 262 than at end effector 276. In some examples, a system implementing method 500 may create a reference position for a different reference point that encompasses the error adjusted prediction determined during process 540. This reference point may then be used to drive the compensating joints to adjust for the disturbances. This works because the disturbance of the point of interest may be represented by a disturbance at other points in a kinematic chain, such as the reference point. The reference position may be determined using one or more reference transforms, such as the reference transforms established during process 520. In some instances, the inverse of the reference transforms may be used. In accordance with FIG. 2, adjusting for movement of end effector 276 may encompass creating a reference manipulator mount 262 position based on the error corrected predicted position of end effector 276 that may be caused by disturbances to set up joints 240 during release of one or more brakes on the set up joints 240.

According to some embodiments, process 570 may be subject to practical limitations. In some examples, the ability of one or more of the compensating joints to compensate for the errors in the position of a point of interest may be limited by range of motion (ROM) limits of the one or more compensating joints. In some examples, when a ROM limit for one or more of the compensating joints is reached and/or is about to be reached, method 500 and/or process 570 may be stopped and an error may be indicated to the operator using one or more visible and/or audible error cues. In some examples, rather than stopping operation of method 500 and/or process 570, process 570 may operate in modified form to partially compensate for movements from a disturbance so as to minimize the controllable error while providing feedback to the operator that not all of the movement caused by the disturbance is being compensated for. In some examples, the feedback may include one or more visible and/or audio cues indicating that compensation is limited and/or the application of resistance on the one or more compensating joints. In some examples, the resistance may include partially applying one or more brakes associated with the one or more compensating joints and/or applying a motion resistance voltage and/or signal in one or more actuators associated with the one or more compensating joints.

As discussed above and further emphasized here, FIG. 5 is merely an example which should not unduly limit the scope of the claims. One of ordinary skill in the art would recognize many variations, alternatives, and modifications.

According to some embodiments, method 500 may be independently applied for each of the instruments being manipulated by the computer-assisted device. In some examples, the instruments may include any of the instruments inserted through a body opening on the patient. In some examples, the compensating joints may be located distal to an arm mounting platform, such as arm mounting platform 227, of the computer-assisted device so that compensation to maintain the placement of end effectors is applied separately for each of the end effectors.

According to some embodiments, the disturbed and compensating joints may not include each of the joints in the articulated arm and/or manipulator. In some examples, the compensating joints may include just the roll, pitch, and yaw joints of the manipulator. In some examples, other joints in the articulated arm and/or the manipulator may be locked to prevent their relative movement during method 500. In some examples, one or more non-actuated joints of the articulated arm and/or the manipulator may be unlocked and/or placed in a float state during method 500 so that disturbances to the placement of the end effector may be at least partially reduced by changes in the unlocked joints. In some examples, the changes in the unlocked joints may reduce the amount that the compensating joints are to be driven. In some examples, the pose of the instrument may be at least partially maintained using resistance from the body wall at the insertion point of the instrument and/or by an operator of the computer-assisted device.

According to some embodiments, one or more of the processes 530-570 may be performed concurrently. According to some embodiments, additional conditions may result in premature termination of method 500 such as by returning control of the computer-assisted device to an operator and/or by suspension of operation of the computer-assisted device. In some examples, the additional conditions may include inability to complete the compensated movement, manual intervention and/or override from an operator using one or more controls on an operator workstation and/or the articulated arms, detection of operator disengagement with the operator workstation using one or more safety interlocks, position tracking errors in the computer-assisted device, system faults, and/or the like. In some examples, the desired movement may not be possible due to the detection of imminent collisions among the links and/or joints of the computer-assisted device, range of motion limits in one or more of the joints of the computer-assisted device, inability to maintain the pose of the instrument due to motion of the patient, and/or the like. In some examples, premature termination of method 500 may result in an error notification being sent to the operator. In some examples, the error notification may include any visual and/or audible indicator, such as a text message, a blinking light, an audible tone, a spoken phrase, and/or the like.

During the disturbance of joints or compensation of disturbances, such as the when implementing method 400 of FIGS. 4 and/or 500 of FIG. 5, it may be beneficial to still allow for teleoperated control of the instruments by an operator. Teleoperated control allows the surgeon to make small adjustments to counteract disturbances and/or in cases where some of the disturbances are not completely accounted for by the disturbance compensation and/or when there is over compensation. Furthermore, a surgeon may continue with a procedure during a disturbance. To aid in the coordination of an operator controlling one or more of the instruments of a system such as instrument 270 of computer aided system 200 of FIG. 2, the system may set up the control system to have an intuitive reference frame.

In some embodiments, an operator views the instruments of computer aided system 200 of FIG. 2 through a display system such as display system 192 of FIG. 1. The display system 192 may be a video stream from a camera, such as an endoscope, that is mounted as an instrument on an articulated arm of computer aided system 200. The camera may display instruments from other articulated arms that may be controlled by controllers, such as input controls 195 of FIG. 1. For the sake of intuitive controls and command of the instruments, the controllers may accept commands in the reference frame of the display, which may be the reference frame of the imaging device/video camera/endoscope.

In some embodiments, when driving joints for compensation or in accordance with user control commands, the movements of the joints may be bandwidth limited, velocity limited, bandwidth controlled, and/or velocity controlled based on the configuration of the articulated arm and the end effector in relation to the articulated arm. For example, with respect to FIG. 2, when end effector 276 is fully extended away from instrument carriage 268, small motions and small velocity movements of the arms from driving one or more joints will cause large movements and faster movements at end effector 276. In contrast, when end effector 276 is fully retracted, large motions and large velocity movements of the arms from driving one or more joints will translate to small movements and slower velocities at end effector 276. Similarly, depending upon how far forward the articulated arm is pitched forward and/or back, yaw rotational movement and velocities will be magnified and/or scaled down.

In some embodiments, driving joints for compensation may be bandwidth limited and/or velocity limited by breaking the compensation movements into several iterative parts. For example, 10 iterative parts over a 0.2 second time span. In this manner, compensation joints may be prevented from conducting large movements in a very short period of time causing additional disturbances to the disturbed joints. For example, when an instrument is close to fully withdrawn, small compensating motions at the end effector may require large motions at one or more of the compensating joints. A fast response by one or more joints for a large motion can jerk the disturbed joint causing an additional disturbance and sometimes a feedback loop between disturbing the disturbed joints during compensation and then compensating for that disturbance, which causes another disturbance. Thus, depending on the orientation of one or more joints and or the end effector, the joints may be velocity limited. In some embodiments, a hard velocity limit may be applied to the joints in all configurations.

Figure 6A:
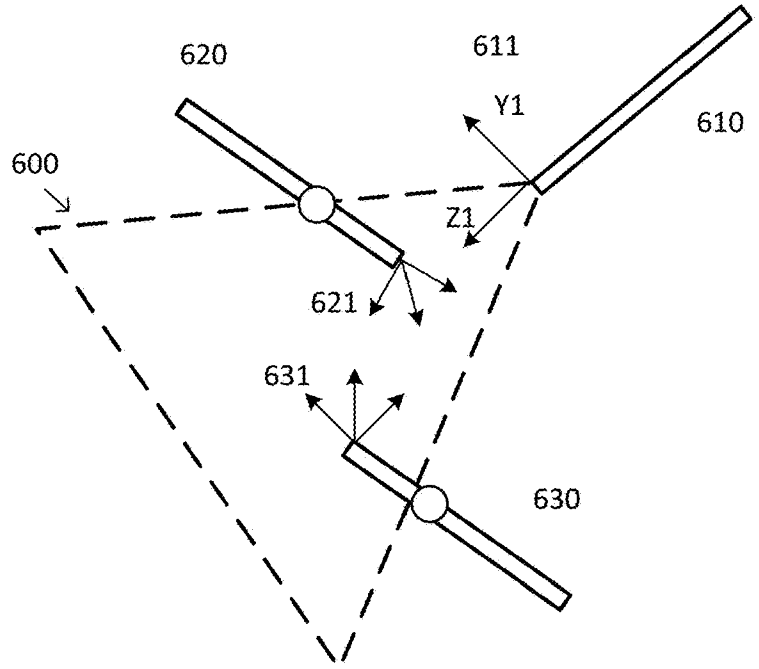
FIG. 6A is a simplified diagram illustrating a perspective view of an exemplary camera view and coordinate systems.
Figure 6B:
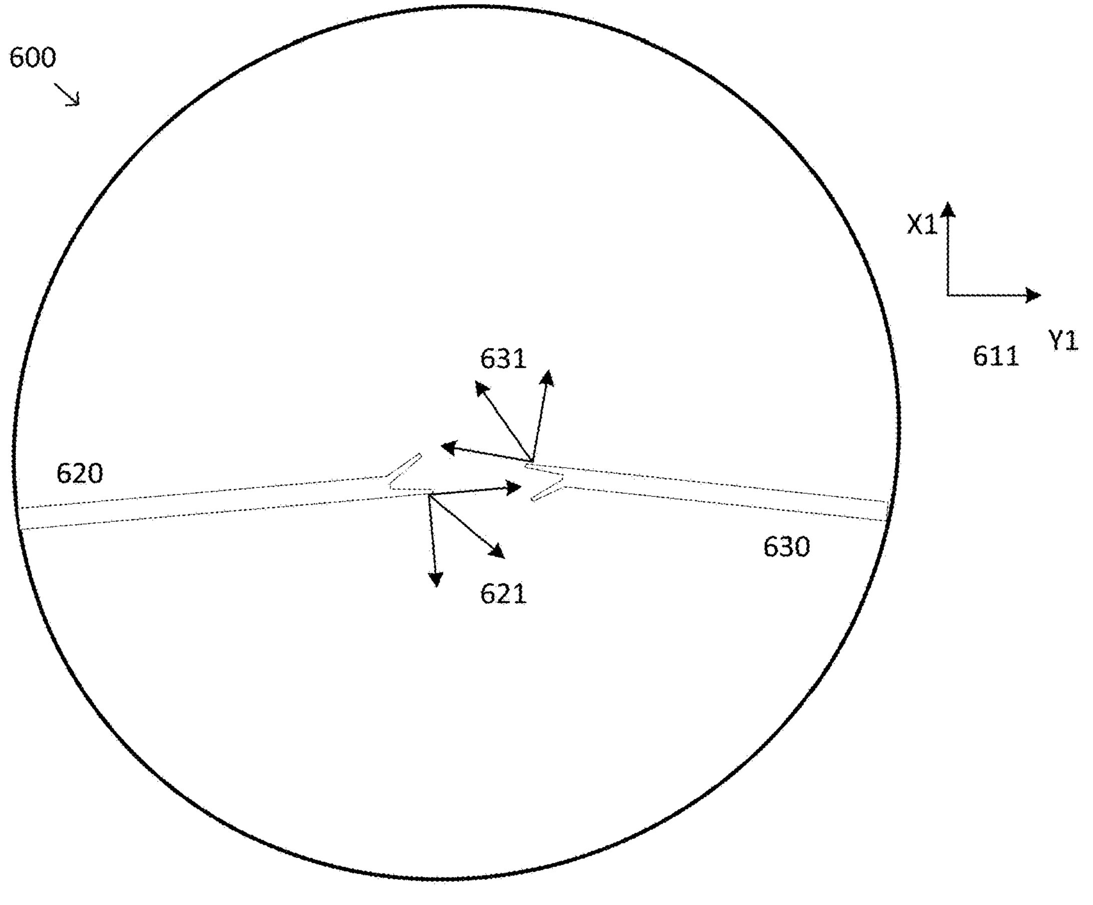
FIG. 6B is a simplified diagram illustrating a camera view from the perspective of a sensor or a display and the related coordinate systems.

FIGS. 6A and 6B illustrates an exemplary camera view 600 from two different perspectives. FIG. 6A is an overhead perspective, and FIG. 6B is the perspective of a sensor of imaging device 610. Camera view 600 from the perspective of FIG. 6B may be viewed from a display, such as display system 192 of operator workstation 190 in FIG. 1, receiving streaming image captures from imaging device 610. In some embodiments, imaging device 610 is an endoscope and controlled by an articulated arm, such as articulate arm 120 of FIG. 1 and/or the articulated arm of FIG. 2. In FIG. 6A, camera view 600 is delineated by the dotted line which may represent an exemplary field of view and focus area for imaging device 610. In FIG. 6B, an exemplary camera view 600 is shown from the perspective of a user viewing a video stream from imaging device 610 on a display, such as display system 192 of operator workstation 190 of FIG. 1. In some embodiments, the video stream provided by imaging device 610 may be stereoscopic. Imaging device 610 may use one or more sensors for providing stereoscopic video streams. In this manner, the operator may have a sense of depth perception when using a system such as computer aided system 100 of FIG. 1. Camera coordinate frame 611 illustrates the coordinate frame of imaging device 610. In FIG. 6A, camera coordinate frame 611 shows the Z1 and Y1 axes of camera coordinate frame 611 with the X1 axis (not shown) going in and out of the page. In FIG. 6B the X1 and Y1 axes of camera coordinate frame 611 are shown with the Z1 axis (not shown) going in and out of the page. In some embodiments, camera coordinate frame 611 may be camera coordinate frame 363 of FIG. 3.

FIGS. 6A and 6B also include instruments 620 and 630, which are controlled by one or more articulated arms, such as articulated arms 120 of FIG. 1 and/or the articulated arm of FIG. 2. Instruments 620 and 630 may be within camera view 600 and may be manipulated by one or more users or operators using controls, such as input controls 195 of FIG. 1, and viewing instruments 620 and 630 from the perspective of FIG. 6B. FIGS. 6A and 6B also illustrate coordinate frames 621 and 631 of instruments 620 and 630, respectively, from different perspectives. In some examples coordinate frames 621 and 631 may be the same as instrument coordinate frames 343 and 353 of FIG. 3.

Because a user teleoperating instruments 620 and 630 may be viewing the instruments from the perspective of FIG. 6B of camera view 600, it may be useful for user commands to be conducted in the camera reference frame 611. Any commands provided in the camera coordinate frame 611 can be translated to commands in the coordinate frames 621 and 631, by using a kinematic model, such as kinematic model 300 of FIG. 3. In this manner, up and down is in relation to the camera view, which may be generally in line of the perspective of the user. A user command to move instrument 620 or 630 up and down may translate to the instrument moving along the X1 axis of camera coordinate frame 611. Similarly, user commands for other translational motions may follow the Y1 and Z1 axes of camera coordinate frame 611. In some embodiments, commands for rotational motions, such as roll, pitch, and yaw, may also be translated from the camera coordinate frame 611 to the coordinate reference frames 621 and 631.

In some embodiments, camera coordinate frame 611 may be detached from the physical imaging device 610. This may be beneficial in some embodiments where the instrument motion is fixed with the camera coordinate frame. For example, if the position of instruments 620 and 630 were commanded in relation to the camera coordinate frame and the camera coordinate frame was fixed to imaging device 610, undesirable disturbances to imaging device 610 would translate into undesirable disturbances to instruments 620 and 630. In some embodiments, a user may have the option to move and/or realign the camera coordinate frame with the imaging device 610. In this manner when imaging device 610 strays too far from camera coordinate frame 611, such as when instrument movements become less intuitive to the user, the user can reset and/or reposition the camera coordinate frame.

In some instances, there may be disturbances to one or more joints of multiple arms affecting the instruments and/or imaging devices of each arm. This may occur, for example, when brakes are released for several joints, such as the staggered brake release discussed in method 400 and/or the brake release of method 500. Furthermore, during a disturbance, it may be desirable to allow a user to maintain intuitive control and operation of one or more of the arms, instruments, and or imaging devices.

Figure 7:
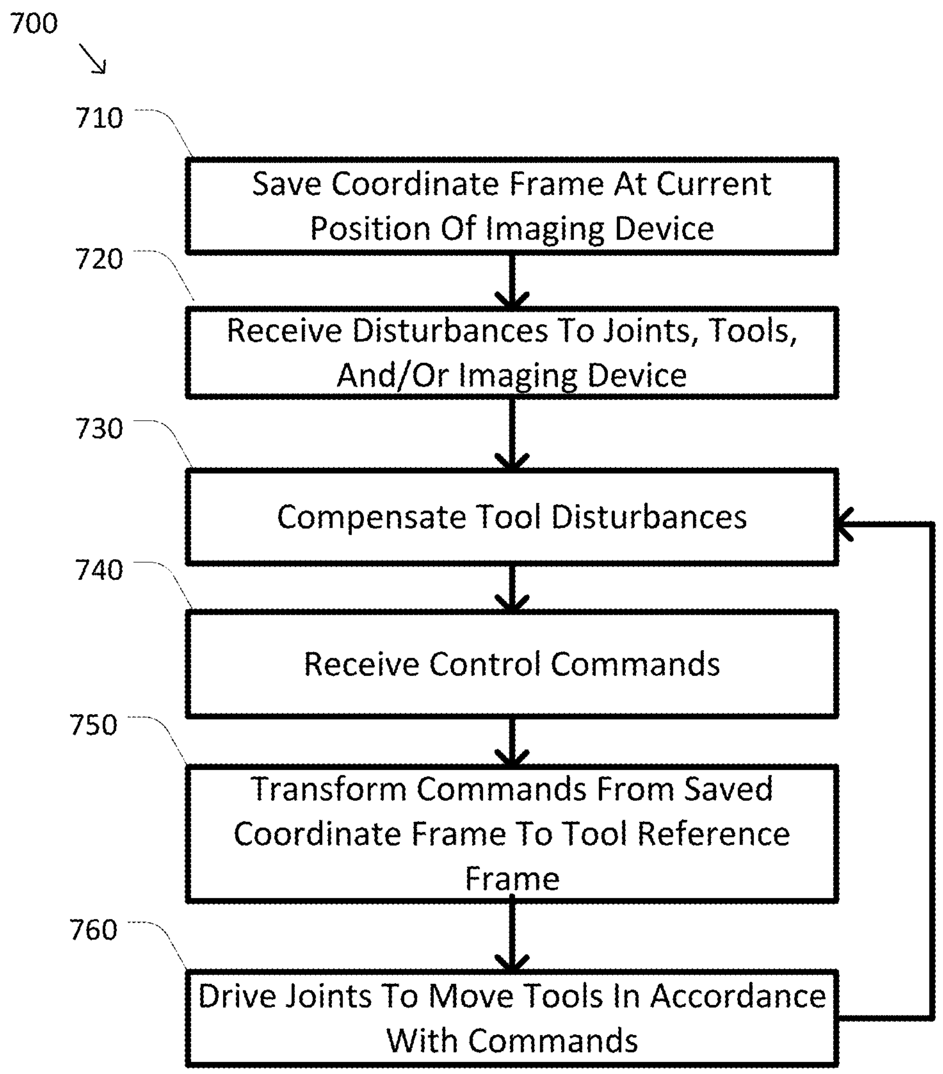
FIG. 7 is a simplified diagram of a method of moving an articulated arm based on user commands while compensating for disturbances to one or more joints in the articulated arm.

FIG. 7 illustrates an exemplary method 700 for maintaining intuitive control of one or more instruments during a disturbance according to some embodiments. In some examples, the disturbance may occur in one or more joints of one or more articulated arms and camera of a computer aided system, such as computer aided system 100 of FIG. 1.

At a process 710, a camera coordinate frame is set at the position of an imaging device. In some embodiments, this is sometimes referred to as "latching" or being "latched." The imaging device may be controlled and/or held by an articulated arm, such as articulated arm 120 of FIG. 1 and/or the articulated arm of FIG. 2. In some embodiments, a camera coordinate frame may be set/latched by recording a transform between a coordinate reference frame to the camera coordinate reference frame at a particular instant of time, such as before a brake release and/or the introduction of a disturbance. In some embodiments, the transform may be determined by using a kinematic model, such as model 300 of FIG. 3. In accordance with FIG. 3, the camera coordinate frame may be camera coordinate frame 363 and the reference frame may be arm mounting platform coordinate frame 330. The recorded transform may be a transform from the reference frame to the camera coordinate frame at a particular point in time with a particular configuration of the articulated arm controlling the imaging device. In some embodiments, recording the transform may include storing the transformation and/or kinematic relationships between the camera coordinate frame and reference coordinate frame on a computer readable medium, such as memory 150 of FIG. 1.

At a process 720, disturbances may be allowed and/or introduced into the system. For example, one or more brakes for one or more joints to one or more articulated arms may be released. This may include the release of brakes on one or more joints of the articulated arm controlling the imaging device and/or instruments. In some embodiments, the disturbances may be caused by the staggered brake release of method 400 and/or the brake release of method 500.

At a process 730, disturbances to the instruments and/or imaging device are compensated for such that the movement of the end effectors and imaging device caused by the disturbance is reduced and/or eliminated. In some embodiments, the compensation conducted at process 730 for each instrument and imaging device may be conducted using one or more of the processes in method 500 of FIG. 5. In some embodiments, the imaging device may be left alone and allowed to be disturbed without compensation.

At a process 740, the computer aided system may receive instrument motion commands. The instrument motion commands may come from a user manipulating controls, such as the input controls 195 of FIG. 1. The instrument motion commands may be received concurrently with a disturbance.

At a process 750, the commands received at process 740 are transformed from the camera coordinate frame recorded during process 710 to the coordinate frame of the respective instruments using the transformation recorded/stored during process 710. In some embodiments the physical imaging device represented by the camera coordinate frame may have been disturbed and moved away, and therefore, no longer in the same position as the camera coordinate frame recorded during 710. In some examples, this difference may result in a reduced level of intuition in control of the instruments, which may be corrected at any time by having the operator reposition the camera using the articulated arm to which it is attached and/or resetting the camera coordinate frame.

At a process 760, the computer aided system drives the joints to move the instruments in accordance with the commands transformed from the camera coordinate frame into the instrument reference frame at process 750. According to some embodiments, one or more of the processes 710-760 may be performed concurrently.

In some embodiments, the process of 760 can occur concurrently with the computer aided system driving the joints to compensate for disturbances. For example, user commands driving the joints may be superimposed onto the commands to drive the joint based on disturbance compensations. The movement of the joints, as discussed above, may be bandwidth limited, velocity limited, bandwidth controlled, and/or velocity controlled. Driving the joints based on user commands super imposed on top of compensating commands may be controlled and/or limited in a similar manner as in the examples discussed above in relation to FIGS. 4 and 5.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A teleoperated device comprising:

a first articulated arm comprising a first plurality of joints, a first plurality of links coupled to the first plurality of joints, and a first plurality of actuators coupled to drive motion of the first articulated arm;

a second articulated arm comprising a second plurality of joints, a second plurality of links coupled to the second plurality of joints, and a second plurality of actuators coupled to drive motion of the second articulated arm; and a control unit comprising one or more hardware processors, the control unit coupled to the first articulated arm and the second articulated arm, wherein the control unit is configured to:

detect a first disturbance to the first articulated arm occurring at a first time, the first disturbance moving an imaging device supported by the first articulated arm away from a first orientation of the imaging device toward a second orientation of the imaging device, and after the first time:

receive a first indication of a first user input to move an end effector supported by the second articulated arm while the imaging device is not at the first orientation, determine, based on the first indication, a first command for moving the end effector as if the imaging device has the first orientation, and command the second plurality of actuators to move the end effector according to the first command.

2. The teleoperated device of claim 1, wherein:

the first disturbance further moves the imaging device away from a first position of the imaging device toward a second position of the imaging device;

the first indication is received while the imaging device is not at the first position; and to determine the first command, the control unit is further configured to determine the first command as if the imaging device has the first position.

3. The teleoperated device of claim 1, wherein the control unit is further configured to determine, prior to the first disturbance, a first coordinate frame based on the first orientation of the imaging device; and wherein to determine the first command, the control unit is configured to determine the first command relative to the first coordinate frame.

4. The teleoperated device of claim 1, wherein the control unit is further configured to:

release one or more brakes of the first articulated arm;

wherein the first disturbance occurs as a result of the release of the one or more brakes.

5. The teleoperated device of claim 1, wherein the first disturbance is caused by movement of a table supporting a patient while the imaging device is inserted through an opening in anatomy of the patient.

6. The teleoperated device of claim 1, wherein the control unit is further configured to:

allow the first disturbance to occur without compensating for movement of the imaging device away from the first orientation.

7. The teleoperated device of claim 1, wherein:

the first plurality of joints comprises one or more first joints and one or more second joints;

the first disturbance is a disturbance to the one or more first joints; and the control unit is further configured to: command, after the first time, one or more actuators of the first plurality of actuators to drive the one or more second joints to move the imaging device back toward the first orientation.

8. The teleoperated device of claim 1, wherein the control unit is further configured to:

after the first time:

receive, after having received an input from an operator to reference movement of the end effector to a current orientation of the imaging device, a second indication of a second user input to move the end effector;

determine, based on the second indication, a second command for moving the end effector based on the imaging device having the current orientation; and command the second plurality of actuators to move the end effector according to the second command.

9. The teleoperated device of claim 1, wherein the first user input corresponds to movement of an input control relative to a display system, the display system configured to display images captured by the imaging device.

10. The teleoperated device of claim 1, wherein:

the second plurality of joints comprises one or more third joints and one or more fourth joints; and the control unit is further configured to:

detect a second disturbance to the one or more third joints, determine a second command to drive the one or more fourth joints to compensate for the second disturbance; and command one or more third actuators of the second plurality of actuators to move the end effector according to the second command.

11. The teleoperated device of claim 10, wherein to determine the second command, the control unit is configured to:

determine an initial position of a point of interest relative to a reference point, the point of interest associated with the end effector;

determine a predicted motion for the point of interest based on the second disturbance; and determine a movement of the one or more fourth joints to move the point of interest in a direction opposite to the predicted motion.

12. The teleoperated device of claim 1, wherein the control unit is further configured to:

superimpose the command to the second plurality of actuators to move the end effector according to the first command and a command to the second plurality of actuators to compensate for a second disturbance to the second articulated arm.

13. A method for controlling a teleoperated device, the method comprising:

detecting, by a control unit comprising one or more hardware processors, a first disturbance to a first articulated arm of the teleoperated device occurring at a first time, the first disturbance moving an imaging device mounted to the first articulated arm away from a first orientation of the imaging device toward a second orientation of the imaging device, the first articulated arm comprising: a first plurality of joints, a first plurality of links coupled by the first plurality of joints, and a first plurality of actuators coupled to drive motion of the first articulated arm; and after the first time:

receiving, by the control unit, a first indication of a first user input to move an end effector supported by a second articulated arm of the teleoperated device while the imaging device is not at the first orientation, the second articulated arm comprising: a second plurality of joints, a second plurality of links coupled by the second plurality of joints, and a second plurality of actuators coupled to drive motion of the second articulated arm;

determining, by the control unit based on the first indication, a first command for moving the end effector as if the imaging device has the first orientation; and commanding, by the control unit, the second plurality of actuators to move the end effector according to the first command.

14. The method of claim 13, wherein:

the first disturbance further moves the imaging device away from a first position of the imaging device toward a second position of the imaging device;

the first indication is received while the imaging device is not at the first position; and determining the first command comprises determining the first command as if the imaging device has the first position.

15. The method of claim 13, further comprising:

allowing, by the control unit, the first disturbance to occur without compensating for movement of the imaging device away from the first orientation.

16. The method of claim 13, wherein:

the first plurality of joints comprises one or more first joints and one or more second joints;

the first disturbance is a disturbance to the one or more first joints; and the method further comprises: commanding, by the control unit after the first time, one or more actuators of the first plurality of actuators to drive the one or more second joints to move the imaging device back toward the first orientation.

17. The method of claim 13, further comprising:

after the first time:

receiving, by the control unit after having received an indication from an operator to reference movement of the end effector to a current orientation of the imaging device, a second indication of a second user input to move the end effector;

determining, by the control unit based on the second indication, a second command for moving the end effector based on the imaging device having the current orientation; and commanding, by the control unit, the second plurality of actuators to move the end effector according to the second command.

18. A non-transitory machine-readable medium comprising a plurality of machine-readable instructions which when executed by one or more hardware processors of a control unit associated with a teleoperated device are adapted to cause the control unit to perform a method comprising:

detecting a first disturbance to a first articulated arm of the teleoperated device occurring at a first time, the first disturbance moving an imaging device mounted to the first articulated arm away from a first orientation of the imaging device toward a second orientation of the imaging device, the first articulated arm comprising: a first plurality of joints, a first plurality of links coupled by the first plurality of joints, and a first plurality of actuators coupled to drive motion of the first articulated arm; and after the first time:

receiving, by the control unit, a first indication of a first user input to move an end effector supported by a second articulated arm of the teleoperated device while the imaging device is not at the first orientation, the second articulated arm comprising: a second plurality of joints, a second plurality of links coupled by the second plurality of joints, and a second plurality of actuators coupled to drive motion of the second articulated arm;

determining, by the control unit based on the first indication, a first command for moving the end effector as if the imaging device has the first orientation; and commanding, by the control unit, the second plurality of actuators to move the end effector according to the first command.

19. The non-transitory machine-readable medium of claim 18, wherein:

the first plurality of joints comprises one or more first joints and one or more second joints;

the first disturbance is a disturbance to the one or more first joints; and the method further comprises: commanding, after the first time, one or more actuators of the first plurality of actuators to drive the one or more second joints to move the imaging device back toward the first orientation.

20. The non-transitory machine-readable medium of claim 18, further comprising:

after the first time:

receiving, after having received an indication from an operator to reference movement of the end effector to a current orientation of the imaging device, a second indication of a second user input to move the end effector;

determining, based on the second indication, a second command for moving the end effector based on the imaging device having the current orientation; and commanding the second plurality of actuators to move the end effector according to the second command.

* * * * *